US009173403B2

(12) United States Patent
Rosentel, Jr. et al.

(10) Patent No.: US 9,173,403 B2
(45) Date of Patent: Nov. 3, 2015

(54) PARASITICIDAL COMPOSITIONS COMPRISING MULTIPLE ACTIVE AGENTS, METHODS AND USES THEREOF

(75) Inventors: Joseph K. Rosentel, Jr., Johns Creek, GA (US); Monica Tejwani, Monmouth Junction, NJ (US); Arima Das-Nandy, Titusville, NJ (US)

(73) Assignee: MERIAL, INC., Duluth, GA (US)

( * ) Notice: Subject to any disclaimer, the term of this patent is extended or adjusted under 35 U.S.C. 154(b) by 100 days.

(21) Appl. No.: 13/078,496

(22) Filed: Apr. 1, 2011

(65) Prior Publication Data

US 2011/0245191 A1     Oct. 6, 2011

Related U.S. Application Data

(60) Provisional application No. 61/320,559, filed on Apr. 2, 2010.

(51) Int. Cl.
| | | |
|---|---|---|
| *A01N 43/90* | (2006.01) | |
| *A01N 43/56* | (2006.01) | |
| *A01N 43/60* | (2006.01) | |
| *A01N 47/02* | (2006.01) | |
| *A01N 49/00* | (2006.01) | |
| *A01N 31/02* | (2006.01) | |

(52) U.S. Cl.
CPC ............... *A01N 43/90* (2013.01); *A01N 31/02* (2013.01); *A01N 43/56* (2013.01); *A01N 43/60* (2013.01); *A01N 47/02* (2013.01); *A01N 49/00* (2013.01)

(58) Field of Classification Search
CPC ... A01N 43/60; A01N 43/90; A01N 2300/00; A01N 25/02; A01N 47/02; A01N 49/00; A01N 43/56; A01N 31/02
See application file for complete search history.

(56) References Cited

U.S. PATENT DOCUMENTS

| | | | |
|---|---|---|---|
| 6,001,858 A | 12/1999 | Sirinyan et al. | 514/341 |
| 6,096,329 A | 8/2000 | Jeannin | 424/405 |
| 6,395,765 B1 | 5/2002 | Etchegaray | |
| 6,426,333 B1 | 7/2002 | Huet et al. | 514/30 |
| 6,797,701 B2 | 9/2004 | Lukas et al. | 514/28 |
| 6,991,801 B2 * | 1/2006 | Soll et al. | 424/406 |
| 7,531,186 B2 | 5/2009 | Boeckh et al. | 424/406 |
| 2003/0166688 A1 | 9/2003 | Soll et al. | |
| 2004/0161441 A1 | 8/2004 | Sirinyan et al. | 424/405 |
| 2004/0167175 A1 | 8/2004 | Soll et al. | 514/341 |
| 2004/0198676 A1 | 10/2004 | Soll et al. | 514/28 |
| 2004/0254125 A1 | 12/2004 | Saito et al. | |
| 2005/0137244 A1 | 6/2005 | Boeckh et al. | |
| 2005/0192319 A1 | 9/2005 | Boeckh et al. | |
| 2008/0031902 A1 | 2/2008 | Lee et al. | |
| 2008/0255037 A1 | 10/2008 | Kanikanti et al. | 514/11 |

FOREIGN PATENT DOCUMENTS

| | | |
|---|---|---|
| BR | PI0403620 A | 3/2006 |
| EP | 836851 A | 4/1998 |
| GB | 2457734 | 8/2009 |
| WO | WO 98/17277 | 4/1998 |
| WO | WO 02/094233 | 11/2002 |
| WO | WO2004/016252 | 2/2004 |
| WO | WO 2007/018659 | 2/2007 |
| WO | WO 2008/030385 | 3/2008 |
| WO | 2008/136791 | 11/2008 |
| WO | WO 2009/018198 | 2/2009 |
| WO | WO 2009/027506 | 3/2009 |
| WO | 2009/112837 | 9/2009 |
| WO | WO 2010/026370 | 3/2010 |
| WO | WO2010/109214 | 9/2010 |

OTHER PUBLICATIONS

Notice of Opposition in the matter of New Zealand Patent Application 595934 in the name of Norbrook Laboratories Limited and Opposition thereto by Merial Limited dated Jun. 28, 2014.
First Supplementary Notice of Opposition in the matter of New Zealand Patent Application 595934 in the name of Norbrook Laboratories Limited and Opposition thereto by Merial Limited dated Aug. 28, 2014.
Second Supplementary Notice of Opposition in the matter of New Zealand Patent Application 595934 in the name of Norbrook Laboratories Limited and Opposition thereto by Merial Limited dated Dec. 11, 2014.
Third Supplementary Notice of Opposition in the matter of New Zealand Patent Application 595934 in the name of Norbrook Laboratories Limited and Opposition thereto by Merial Limited dated Dec. 16, 2014.
First Supplementary Statement of Case in the matter of New Zealand Patent Application 595934 in the name of Norbrook Laboratories Limited and Opposition thereto by Merial Limited dated Dec. 11, 2014.
"Fipronil (354)", Pesticide Manual thirteenth edition 2003, British Crop Protection Council.
Lyons et al., "Critical and controlled tests of activity of moxidectin (cl 301,423) against natural infections of internal parasites of equids," Veterinary Parasitology, 1992, vol. 41, No. 3-4, pp. 255-284.
De Souza Dias et al., "Use of praziquantel in patients with *Schistosomiasis mansoni* previously treated with oxamniquine and/or hycanthone: resistance of *Schistosoma mansoni* to schistosomicidal agentsTransactions," Transactions of the Royal Society of Tropical Medicine and Hygiene, vol. 76, No. 5, Jan. 1, 1982, pp. 652-659.

(Continued)

*Primary Examiner* — Kara R McMillian
(74) *Attorney, Agent, or Firm* — Judy Jarecki-Black; John Ezcurra; Merial, Inc.

(57) ABSTRACT

This invention relates to compositions for combating ectoparasites and endoparasites in animals, comprising at least one 1-arylpyrazole, at least one macrocyclic lactone, at least one insect growth regulator, and at least one anthelmintic compound in combination with a pharmaceutically acceptable carrier. This invention also provides for an improved methods for eradicating, controlling, and preventing parasite infections and infestations in an animal comprising administering the compositions of the invention to the animal in need thereof.

9 Claims, 1 Drawing Sheet

(56) References Cited

OTHER PUBLICATIONS

Bianciardi P. & Otranto D., "Treatment of dog thelaziosis caused by *Thelazia callipaeda* (Spirurida, *Thelaziidae*) using a topical formulation of imidacloprid 10% and moxidectin 2.5%," Veterinary Parasitology, 2005, vol. 129, No. 1-2, pp. 89-93.

Hubert et al., "Persistent efficacy of topical moxidectin against *Dictyocaulus viviparus* and Ostertagia ostertagi," Veterinary Parasitology, 1997, vol. 68, No. 1-2, pp. 187-190.

Charles et al., "Evaluation of the efficacy of emodepside + praziquantel topical solution against cestode (*Dipylidium caninum*, *Taenia taeniaeformis*, and *Echinococcus multilocularis*) infections in cats," Parasitol Res., 2005, vol. 97, Suppl. 1, pp. S33-40.

The Merck Index, Fourteenth Edition 2006, p. 1325.

Liu et al., "Investigation of the Phase Diagrams of Chiral Praziquantel," Chirality, 2006, 18, 259-264.

Seubert et al., "Synthesis and properties of praziquantel, a novel broad spectrum anthelmintic with excellent activity against Schistosomes and Cestodes," Experientia, 1977, vol. 8, issue 8, pp. 1037-1037.

U.S. EPA Factsheet for Fipronil, dated May 1996.

"Efficacy of fipronil/(S)-methoprene combination spot-on for dogs against shed eggs, emerging and existing adult cat fleas (*Ctenocephalides felis*, Bouche)," D.R. Young, P.C. Jeannin, A. Boeckh; Veterinary Parasitology 125 (2004) 397-407.

Statement of Case in the matter of New Zealand Patent Application 595934 in the name of Norbrook Laboratories Limited and Opposition thereto by Merial Limited; Aug. 28, 2014.

CAPlus Document No. 146:169274: "Transdermal cestodicide for use with or without other anthelmintics and ectoparasiticides or insect growth inhibitors for treatment of dogs, cats, and horses"; Feb. 8, 2007.

First Amended Statement of Grounds and Particulars in the matter of Australian Patent Application No. 2010227340 in the name of Norbrook Laboratories Limited and Opposition thereto by Merial Limited dated Apr. 8, 2015.

Second Supplementary Statement of Case in the matter of New Zealand Patent Application No. 595934 in the name of Norbrook Laboratories Limited and Opposition thereto by Merial Limited dated Apr. 30, 2015.

Fourth Supplementary Notice of Opposition in the matter of New Zealand Patent Application No. 595934 in the name of Norbrook Laboratories Limited and Opposition thereto by Merial Limited dated Apr. 30, 2015.

Declaration of Jeffrey N. Clark, D.V.M., Ph.D. In the matter of Australian Patent Application No. 2010227340 in the name of Norbrook Laboratories Limited and Opposition thereto by Merial Limited dated Mar. 18, 2015.

Declaration of James E. Pate, Ph.D. In the matter of Australian Patent Application No. 2010227340 in the name of Norbrook Laboratories Limited and Opposition thereto by Merial Limited dated Mar. 18, 2015.

Declaration of Joe R. Pippia in the matter of Australian Patent Application No. 2010227340 in the name of Norbrook Laboratories Limited and Opposition thereto by Merial Limited dated Mar. 19, 2015.

Declaration of Professor Jonathan Hadgraft in the matter of Australian Patent Application No. 2010227340 in the name of Norbrook Laboratories Limited and Opposition thereto by Merial Limited dated Mar. 18, 2015.

Declaration of Professor Joel L. Zatz in the matter of Australian Patent Application No. 2010227340 in the name of Norbrook Laboratories Limited and Opposition thereto by Merial Limited dated Mar. 16, 2015.

Summary of Product Characteristics for Frontline Spray 0.25% w/v from Irish Health Products Regulatory Authority. Date of first authorization/renewal of the authorization Jul. 7, 2007.

Summary of Product Characteristics for Frontline Spot on Dog from Irish Medicines Board. Date of first authorization/renewal of the authorization Oct. 17, 2008. Date of revision of text Nov. 13, 2008.

Summary of Product Characteristics for Frontline Spot on Dog from the U.K. Veterinary Medicines Directorate. Date of first authorization/renewal of the authorization Nov. 27, 2006. Date of revision of text Mar. 2010.

Product label for Frontline Top Spot for Small Dogs up to 10 kg. Merial Australia PTY Ltd.

Summary of Product Characteristics for Frontline Combo Spot on Cat from Irish Medicines Board. Date of first authorization/renewal of the authorization Sep. 26, 2008. Date of revision of text Oct. 2012.

Summary of Product Characteristics for Advantage 100 Spot-on Solution for Dogs from the U.K. Veterinary Medicines Directorate. Date of first authorization/renewal of the authorization Mar. 17, 1997. Date of revision of text Jan. 2011.

Summary of Product Characteristics for Advantix Spot-on Solution for Dogs over 25 kg from the U.K. Veterinary Medicines Directorate. Date of first authorization/renewal of the authorization Dec. 23, 2003. Date of revision of text Dec. 2011.

Summary of Product Characteristics for Profender Spot-on Solution for Cats from the European Medicines Agency. Date of first authorization/renewal of the authorization Jul. 17, 2005. Date of revision of text Jul. 1, 2010.

Summary of Product Characteristics for Aludex 50 g/1 Concentrate for cutaneous solution from the Irish Medicines Board. Date of first authorization/renewal of the authorization Sep. 30, 2009. Date of revision of text Apr. 2013.

MSDS for Advocate for Cats from Bayer Healthcare. Creation date Jun. 25, 2003. Revision date Sep. 23, 2003.

MSDS for Advantix for Dogs from Bayer Healthcare. Creation date Jul. 27, 2003. Revision date Feb. 7, 2007.

MSDS for Revolution single dose tubes from Pfizer Inc. Revision date May, 11, 2004.

MSDS for Profender from Bayer Healthcare. Date of issue: Aug. 3, 2008.

MSDS for Defend Exspot for Dogs from Schering Plough Animal Health Corporation. Published Sep. 10, 2004.

MSDS for Frontline Plus for Dogs from Merial. Printing date Oct. 23, 2001.

MSDS for Advocate for Cats from Bayer Healthcare. Creation date Jun. 23, 2003. Revision date Sep. 23, 2003.

MSDS for Profender for Cats from Bayer Australia Ltd. Creation date Jul. 1, 2004. Revision date Mar. 22, 2012.

MSDS for Revolution from Pfizer Australia Pty Ltd. Creation date Jun. 2004.

* cited by examiner

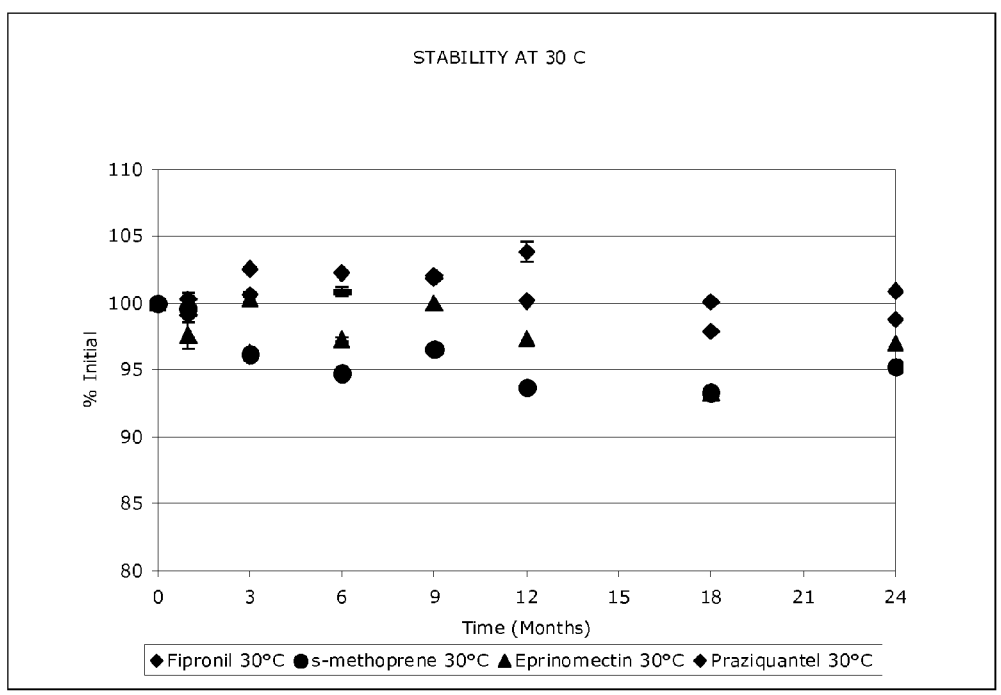

PARASITICIDAL COMPOSITIONS COMPRISING MULTIPLE ACTIVE AGENTS, METHODS AND USES THEREOF

CROSS REFERENCE TO RELATED APPLICATIONS

This application claims the benefit of priority to U.S. Provisional Application No. 61/320,559 filed Apr. 2, 2010, which is incorporated herein by reference in its entirety.

FIELD OF THE INVENTION

The present invention provides veterinary compositions comprising at least one 1-arylpyrazole active agent, at least one macrocyclic lactone active agent, at least one insect growth regulator (IGR) active agent, and at least one anthelmintic active agent for controlling ectoparasites and endoparasites in animals; the use of these compositions against ectoparasites and endoparasites, and methods for preventing or treating parasitic infections and infestations in animals.

BACKGROUND OF THE INVENTION

Animals such as mammals and birds are often susceptible to parasite infestations/infections. These parasites may be ectoparasites, such as insects, and endoparasites such as filariae and other worms. Domesticated animals, such as cats and dogs, are often infested with one or more of the following ectoparasites:

fleas (e.g. *Ctenocephalides* spp., such as *Ctenocephalides* felts and the like), ticks (e.g. *Rhipicephalus* spp., *Ixodes* spp., *Dermacentor* spp., *Amblyoma* spp., and the like), mites (e.g. *Demodex* spp., *Sarcoptes* spp., *Otodectes* spp., and the like), lice (e.g. *Trichodectes* spp., *Cheyletiella* spp., *Lignonathus* spp. and the like), mosquitoes (*Aedes* spp., *Culux* spp., *Anopheles* spp. and the like) and flies (*Hematobia* spp., *Musca* spp., *Stomoxys* spp., *Dematobia* spp., *Coclyomia* spp. and the like).

Fleas are a particular problem because not only do they adversely affect the health of the animal or human, but they also cause a great deal of psychological stress. Moreover, fleas are also vectors of pathogenic agents in animals and humans, such as dog tapeworm (*Dipylidium caninum*).

Similarly, ticks are also harmful to the physical and psychological health of the animal or human. However, the most serious problem associated with ticks is that they are the vector of pathogenic agents in both humans and animals. Major diseases which are caused by ticks include borrelioses (Lyme disease caused by *Borrelia burgdorferi*), babesioses (or piroplasmoses caused by *Babesia* spp.) and rickettsioses (also known as Rocky Mountain spotted fever). Ticks also release toxins which cause inflammation or paralysis in the host. Occasionally, these toxins are fatal to the host.

Likewise, farm animals are also susceptible to parasite infestations. For example, cattle are affected by a large number of parasites. A parasite which is very prevalent among farm animals is the tick genus *Boophilus*, especially those of the species *microplus* (cattle tick), *decoloratus* and *annulatus*. Ticks, such as *Boophilus microplus*, are particularly difficult to control because they live in the pasture where farm animals graze.

Animals and humans also suffer from endoparasitical infections including, for example, helminthiasis which is most frequently caused by a group of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichiris, Enterobius* and parasites which are found in the blood or other tissues and organs such as filarial worms and the extra intestinal stages of *Strogyloides, Toxocara* and *Trichinella*

1-arylpyrazoles as a class of chemicals are well known in the art, and certain compounds in this class have been found to be potently active against a wide range of pests and parasites that are harmful to animals and plants. For example, 1-arylpyrazole derivatives are known in the art to prevent, treat or control ectoparasitic infestations in mammals, such as cats, dogs and cattle. Certain 1-arylpyrazoles and their use against pests are described in US Patent Publication Nos. US 2005/0182048; US 2006/0135778; US 2008/0132487; US 2008/0031902; U.S. Pat. Nos. 4,963,575; 5,122,530; 5,232, 940; 5,236,938; 5,246,255; 5,547,974; 5,567,429; 5,576,429; 5,608,077; 5,714,191; 5,814,652; 5,885,607; 5,567,429; 5,817,688; 5,885,607; 5,916,618; 5,922,885; 5,994,386; 6,001,384; 6,010,710; 6,057,355; 6,069,157; 6,083,519; 6,090,751; 6,096,329; 6,124,339; 6,180,798; 6,335,357; 6,350,771; 6,372,774; 6,395,906; 6,413,542; 6,685,954; and 7,468,381. See also: EP 0 234 119, EP 0 295 117, EP 0 352 944, EP 0 500 209, EP 0 780 378, EP 0 846 686, and EP 0 948 485, all of which are incorporated herein by reference in their entirety.

The compounds of the families defined in these patents are extremely active and one of these compounds, 5-amino-3-cyano-1-(2,6-dichloro-4-trifluoromethylphenyl)-4-trifluoromethylsulfinylpyrazole, or fipronil, is particularly effective against pests, including fleas and ticks.

These compounds are described as having activity against a very large number of parasites, including insects and acarines in fields as varied as agriculture, public health and veterinary medicine. The general teaching of these documents indicates that these active compounds may be administered via different routes: oral, parenteral, percutaneous and topical routes. Topical administration comprises, in particular, skin solutions (pour-on or spot-on), sprays, drenches, baths, showers, jets, powders, greases, shampoos, creams, etc. The pour-on type skin solutions may be designed for percutaneous administration.

Other compounds that are known in the art to prevent, treat or control endo- and ectoparasitic infestations include milbemycin or avermectin derivatives, which are natural or semi-synthetic compounds that contain a 16-membered macrocyclic ring. The avermectin and milbemycin series of compounds are potent anthelmintic and antiparasitic agents against a wide range of internal and external parasites. The natural product avermectins are disclosed in U.S. Pat. No. 4,310,519 to Albers-Schonberg, et al., and the 22,23-dihydro-avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Naturally occurring milbemycins are described in Aoki et al., U.S. Pat. No. 3,950, 360.

US 2008/031902 describes certain 1-arylpyrazole compounds that are substituted at the 5-position of the pyrazole ring with alkyl or $C_1$-$C_4$ haloalkyl groups. These compounds were also found to be particularly effective against fleas and ticks.

U.S. Pat. Nos. 6,096,329 and 6,685,954, both incorporated herein by reference, describe synergistic combinations of 1-arylpyrazole compounds and an Insect Growth Regulator (IGR) active agent, such as (S)-methoprene that are highly efficacious against ectoparasites.

Other pharmaceutical or therapeutic agents are those known in the art to treat parasitic infection caused by nematodes and trematodes. In order to treat cestode (and trematode) infections in warm-blooded animals, it is known, to administer 2-acyl-4-oxo-pyrazino-isoquinoline derivatives to the animal (see, e.g., U.S. Pat. No. 4,001,441, herein incorporated by reference). A compound of this class that is often used to treat cestode and nematode infections is praziquantel, which has the following structure:

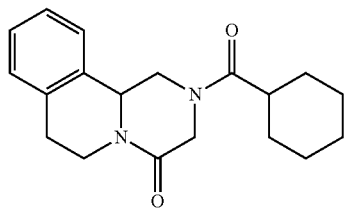 [SMILES: O=C(C1CCCCC1)N1CC(=O)N2CCc3ccccc3C2C1]

Praziquantel may be used in the treatment of endoparasitic infections including infections by liver flukes or *schistosoma*. Praziquantel works by causing severe spasms and paralysis of the worm's muscles.

U.S. Pat. Nos. 6,482,425; 6,426,333; 6,962,713 and 6,998,131, all incorporated by reference in their entirety, describe compositions comprising combinations of arylpyrazole compounds and macrocyclic lactone active agents that are effective against ectoparasites and endoparasites.

Notwithstanding the compositions comprising arylpyrazole active agents alone or in combination with other active agents described in the documents above, there is a need for veterinary compositions and methods with improved efficacy and spectrum of coverage to protect animals against both endoparasites and ectoparasites.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention provides compositions and formulations comprising at least one 1-arylpyrazole compound in combination with at least one macrocyclic lactone compound, at least one insect growth regulator compound, and at least one anthelmintic compound; uses or veterinary uses thereof for the treatment or prophylaxis of parasitic infections and infestations of animals (either wild or domesticated), including livestock and companion animals such as cats, dogs, horses, chickens, sheep, goats, pigs, turkeys and cattle, with the aim of ridding these hosts of parasites commonly encountered by such animals. In preferred embodiments, the topical veterinary composition of the invention are advantageously in the form of a spot-on or a pour-on formulation for application to localized areas on the animal to be treated.

The invention also provides methods for the treatment or prevention of parasitic infections and infestations in animals, comprising administering an effective amount of a composition comprising at least one 1-arylpyrazole in combination with at least one macrocyclic lactone compound, at least one IGR compound, and at least one anthelmintic active agent to the animal. Surprisingly, it has been found that the inventive compositions and formulations described herein exhibit superior broad spectrum efficacy against harmful endoparasites and ectoparasites over a long duration compared to compositions known in the art.

In one embodiment, the invention provides topical veterinary compositions comprising effective amounts of at least one 1-arylpyrazole of formula (I) or formula (IA) below where variables X, $R_1$, $R_2$, $R_{2a}$, $R_3$, $R_{3a}$, $R_4$, $R_{4a}$, $R_5$, $R_6$, $R_{6a}$ $R_7$, and $R_{13a}$ are as defined herein, in combination with at least one IGR active agent, at least one macrocyclic lactone active agent and at least one anthelmintic active agent and a pharmaceutically or veterinarily acceptable liquid carrier.

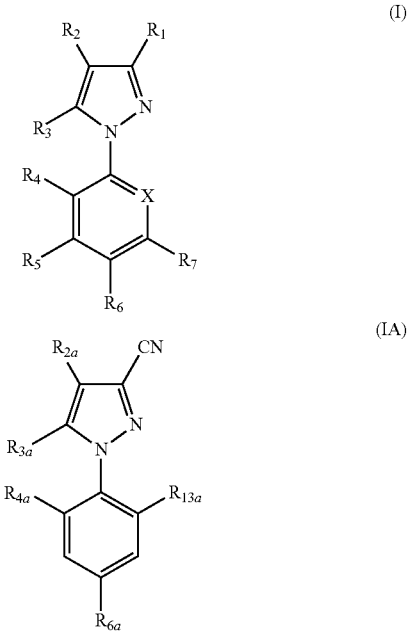

In some preferred embodiments, the topical veterinary compositions and methods comprise fipronil. In other preferred embodiments, the macrocyclic lactone active agent is an avermectin or a milbemycin active agent including, but not limited to, eprinomectin, ivermectin, selamectin, milbemectin, milbemycin D, milbemycin oxime, or moxidectin.

In other preferred embodiments, the compositions and methods of the invention comprise the IGR active agents (S)-methoprene, pyriproxyfen, hydroprene, cyromazine, fluazuron, lufenuron, or novaluron. In other embodiments, the compositions and methods comprise at least one of thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, or an aryloazol-2-yl cyanoethylamino active agent.

In some embodiments, the topical veterinary composition of the invention may comprise a $C_1$-$C_{10}$ alcohol or ester, a $C_{10}$-$C_{18}$ saturated fatty acid or esters, a $C_{10}$-$C_{18}$ monounsaturated fatty acid or ester, a monoester or diester of an aliphatic diacid, a glycerol monoesters, a glycerol diester, a glycerol triester, a glycol, a glycol ether, a glycol ester, a glycol carbonate, a polyethylene glycol, a polyethylene glycol monoether, a polyethylene glycol diether, a polyethylene glycol monoester, a polyethylene glycol diester, or a mixture thereof as components in the pharmaceutically or veterinarily acceptable carrier or diluent. In other embodiments, the compositions may include acetone, acetonitrile, benzyl alcohol, ethanol, isopropanol, diisobutyl adipate, diisopropyl adipate, glycerol formal, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, dimethyl isosorbide, 2-pyrrolidone, N-methylpyrrolidone, diethylene glycol monoethyl ether, triacetin, butyl acetate, octyl acetate, propylene carbonate, butylene carbonate, dimethyl sulfoxide, dimethylformamide, dimethylacetamide, or any combination thereof in the pharmaceutically or veterinarily acceptable carrier or diluent.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWING

The single FIGURE is a graph of the stability of one of the formulations of the invention containing four active agents in a carrier comprising glycerol formal and dimethyl isosorbide at 30° C. for up to 24 months.

DETAILED DESCRIPTION

The present invention provides novel and inventive compositions comprising at least one 1-arylpyrazole compound in combination with at least one macrocyclic lactone compound, at least one insect growth regulator (IGR), and at least one anthelmintic compound together with a pharmaceutically acceptable carrier or diluent.

The compositions of the invention can be in a variety of forms suitable for different forms of administration including, but are not limited to, oral formulations, injectable formulations, and topical, dermal or subdermal formulations.

In some embodiments of the invention, the compositions are preferably in a form that is suitable for topical administration, which includes spot-on formulations that are applied to a localized area on an animal. Topical pour-on formulations are also encompassed by the invention. These formulations provide surprisingly effective protection of the animals against both ectoparasites and endoparasites for an extended period of time.

In one aspect, the invention provides topical compositions comprising at least one 1-arylpyrazole compound in combination with at least one macrocyclic lactone compound, at least one IGR active agent, and at least one anthelmintic compound together with a pharmaceutically acceptable carrier or diluent.

In one embodiment, the compositions of the invention comprise at least one avermectin or milbemycin compound. In another embodiment, the at least one avermectin or milbemycin compound included in the compositions is abamectin, dimadectin, doramectin, emamectin, eprinomectin, ivermectin, latidectin, lepimectin, selamectin, milbemectin, milbemycin D, moxidectin or nemadectin.

Also provided are methods and uses for the treatment and/or prophylaxis of parasitic infections and infestations of animals, comprising administering an effective amount of a formulation of the invention to the animal.

The invention includes at least the following features:

(a) The invention provides novel compositions that exhibit superior activity against animal parasites comprising at least one 1-arylpyrazole compound in combination with at least one macrocyclic lactone compound, at least one IGR, and at least one anthelmintic active agent, or pharmaceutically acceptable salts, solvates or hydrates thereof, together with a pharmaceutically acceptable carrier or diluent;

(b) topical veterinary formulations that exhibit superior activity against animal parasites comprising at least one 1-arylpyrazole compound in combination with at least one macrocyclic lactone active agent, at least one IGR, and at least one anthelmintic compound, or pharmaceutically acceptable salts, solvates or hydrates thereof, together with a pharmaceutically acceptable carrier or diluent;

(c) veterinary compositions comprising fipronil in combination with at least one macrocyclic lactone active agent, at least one insect growth regulator (IGR), and at least one anthelmintic compound, or pharmaceutically acceptable salts, solvates or hydrates thereof, and a pharmaceutically acceptable carrier or diluent;

(d) veterinary compositions comprising fipronil in combination with at least one of abamectin, dimadectin, doramectin, emamectin, eprinomectin, ivermectin, latidectin, lepimectin, selamectin, milbemectin, milbemycin D, moxidectin or nemadectin, at least one insect growth regulator (IGR), and at least one anthelmintic compound, or pharmaceutically acceptable salts, solvates or hydrates thereof, and a pharmaceutically acceptable carrier or diluent;

(e) veterinary composition comprising fipronil in combination with at least one of abamectin, dimadectin, doramectin, emamectin, eprinomectin, ivermectin, latidectin, lepimectin, selamectin, milbemectin, milbemycin D, moxidectin or nemadectin, at least one IGR compound which mimics juvenile hormones or which inhibits chitin synthesis, and at least one anthelmintic compound, or pharmaceutically acceptable salts, solvates or hydrates thereof, and a pharmaceutically acceptable carrier or diluent;

(f) topical spot-on veterinary formulations, comprising fipronil in combination with at least one of abamectin, dimadectin, doramectin, emamectin, eprinomectin, ivermectin, latidectin, lepimectin, selamectin, milbemectin, milbemycin D, moxidectin or nemadectin, at least one IGR compound which mimics juvenile hormones or which inhibits chitin synthesis, and at least one anthelmintic compound, or pharmaceutically acceptable salts, solvates or hydrates thereof, and a pharmaceutically acceptable carrier or diluent;

(g) methods for the treatment or prevention of parasitic infections and infestations in an animal comprising administering an effective amount of a composition comprising at least one 1-arylpyrazole compound in combination with at least one macrocyclic lactone active agent, at least one IGR compound, and at least one anthelmintic active agent, or pharmaceutically acceptable salts, solvates or hydrates thereof, together with a pharmaceutically acceptable carrier or diluent;

(h) use of veterinary compositions comprising at least one 1-arylpyrazole compound in combination with at least one macrocyclic lactone active agent, at least one IGR, and at least one anthelmintic compound, or pharmaceutically acceptable salts, solvates or hydrates thereof, together with a pharmaceutically acceptable carrier or diluent in the prevention or treatment of animal parasites.

In this disclosure and in the claims, terms such as "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

It is also noted that in this disclosure and in the claims and/or paragraphs, the compounds of the invention are intended to include all stereoisomers and crystalline forms (which includes hydrated forms, polymorphic forms and amorphous forms with up to 15% by weight crystalline structure) thereof.

DEFINITIONS

Terms used herein will have their customary meaning in the art unless specified otherwise. The organic moieties mentioned in the definitions of the variables of formula (I) or (IA) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals, including humans. Animals include, but are not limited to, humans, cats, dogs, cattle, chickens, cows, deer, goats, horses, llamas, pigs, sheep and yaks. It also includes an individual animal in all stages of development, including embryonic and fetal stages.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1, 2-trimethyl-2-propenyl, 1-ethyl-1-methyl-2-propenyl, 1-ethyl-2-methyl-1-propenyl and 1-ethyl-2-methyl-2-propenyl.

"Cycloalkenyl" refers to monovalent cyclic alkenyl groups of from 4 to 10 carbon atoms, preferably 5 to 8 carbon atoms, having single or multiple condensed rings which condensed rings may or may not be cycloalkenyl provided that the point of attachment is to a cycloalkenyl ring atom. Examples of cycloalkenyl groups include, by way of example, cyclopenten-4-yl, cyclooctene-5-yl and the like. Alkenyl and cycloalkenyl groups may be unsubstituted or substituted with one or more substituents as described for alkyl above.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—$CH_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Alkoxycarbonyl refers to —C(=O)—O-alkyl, wherein alkoxy is as defined above;

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$)).

Stereoisomers and Polymorphic Forms

It will be appreciated by those of skill in the art that certain compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents.

Salts

Also contemplated within the scope of the invention are acid or base salts, where applicable, of the compounds of the invention provided for herein.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts (NH4$^+$), alkyl- and dialkylammonium salts, and salts of cyclic amines such as the morpholine and piperidine salts.

1-arylpyrazoles as a class of chemicals are well known in the art, and certain compounds in this class have been found to be potently active against a wide range of pests and parasites that are harmful to animals and plants. For example, 1-arylpyrazole derivatives are known in the art to prevent, treat or control ectoparasitic infestations in mammals, such as cats, dogs and cattle. Certain 1-arylpyrazoles and their use against pests are described in US Patent Publication Nos. US 2008/0132487 and US 2008/0031902; U.S. Pat. Nos. 4,963,575; 5,122,530; 5,232,940; 5,236,938; 5,246,255; 5,547,974; 5,567,429; 5,576,429; 5,608,077; 5,714,191; 5,814,652; 5,885,607; 5,567,429; 5,817,688; 5,885,607; 5,916,618; 5,922,885; 5,994,386; 6,001,384; 6,010,710; 6,057,355; 6,069,157; 6,083,519; 6,090,751; 6,096,329; 6,124,339; 6,180,798; 6,335,357; 6,350,771; 6,372,774; 6,395,906; 6,413,542; 6,685,954; and 7,468,381, 7,517,877, and 7,514,561; and European Patent Publications Nos. EP 0 234 119, EP 0 295 117, EP 0 352 944, EP 0 500 209, EP 0 780 378, EP 0 846 686, and EP 0 948 485, all of which are incorporated herein by reference in their entirety.

The compounds of the families defined in these patents are extremely active and one of these compounds, 5-amino-3-cyano-1-(2,6-dichloro-4-trifluoromethylphenyl)-4-trifluoromethylsulfinylpyrazole, or fipronil, is particularly effective against pests, including fleas and ticks.

In one embodiment, the invention provides compositions that comprise at least one 1-arylpyrazole compound of formula (I):

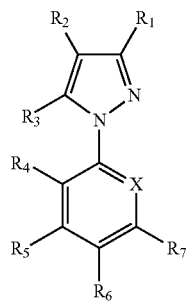
(I)

wherein:
R$_1$ is hydrogen, cyano, nitro, halogen, R$_3$, R$_8$, formyl, —C(O)R$_8$, —C(O)OR$_8$, —C(O)NR$_9$R$_{10}$, —C(=NOH)NH$_2$, —C(=NNH$_2$)R$_9$, or —C(S)NH$_2$;

R$_2$ is R$_8$, halogen, cyano, nitro, —SCN, 4-5-dicyanoimidazol-2-yl, or —S(O)$_m$R$_{11}$;

R$_3$ is hydrogen, halogen, alkyl, haloalkyl, OH, OR$_8$, S(O)$_m$R$_{11}$, —C(O)R$_8$, —C(O)OR$_8$, NR$_9$R$_{10}$, —N=C(R$_9$)(R$_{14}$), —N=C(R$_{10}$)—Z—(R$_9$), —N=C(R$_{10}$)—NR$_9$R$_{10}$, —N(R$_8$)—C(R$_{10}$)=NR$_9$, —N(R$_{11}$)C(O)CR$_{15}$R$_{10}$R$_{11}$, —N(R$_{11}$)C(O)aryl, —N(R$_{11}$)C(O)heteroaryl or —N(R$_{11}$)C(O)OR$_{10}$;

R$_4$, R$_5$ and R$_7$ are independently hydrogen, halogen, alkyl, haloalkyl, cyano or nitro;

R$_6$ is halogen, alkyl, haloalkyl, alkoxy, haloalkyloxy, cyano, nitro, —C(O)R$_{12}$, —S(O)$_n$R$_{12}$ or SF$_5$;

X is a nitrogen atom or C—R$_{13}$;

Z is O, S(O)$_m$ or NR$_9$

R$_8$ is alkyl or haloalkyl;

R$_9$ is hydrogen, alkyl, haloalkyl or alkoxy;

R$_{10}$ is hydrogen, alkyl, haloalkyl, alkoxy, or —C(O)R$_8$;

R$_{11}$ is alkyl, haloalkyl, alkenyl, haloalkenyl, alkynyl, haloalkynyl, alkoxyalkyl, or haloalkoxyalkyl;

R$_{12}$ is alkyl or haloalkyl;

R$_{13}$ is hydrogen, halogen, cyano, nitro, alkyl, haloalkyl, alkoxy or haloalkoxy;

R$_{14}$ is optionally substituted aryl or optionally substituted heteroaryl;

R$_{15}$ is hydrogen, halogen, alkoxy, haloalkoxy, alkoxyalkyl, haloalkoxyalkyl, formyloxy, alkylcarbonyloxy, haloalkylcarbonyloxy, alkylthio, haloalkylthio, alkylsulfinyl, haloalkylsulfinyl, alkylsulfonyl, haloalkylsulfonyl, alkylamino, dialkylamino, haloalkylamino, di(haloalkyl)amino, aryloxy or arylalkoxy;

wherein said alkyl, haloalkyl, alkoxy, groups are optionally substituted with alkyl, haloalkyl, alkoxy, aryl, or heteroaryl; said aryl or heteroaryl groups are optionally substituted with one or more of alkyl, haloalkyl, aryl, halogen, C(O)R$_8$, —C(O)OR$_8$, —C(O)NR$_9$R$_{10}$, —C(S)NH$_2$, or —S(O)$_m$R$_{11}$ m is 0, 1 or 2; and n is 0, 1 or 2; or a pharmaceutically acceptable salt, hydrate or solvate thereof;

in combination with at least one macrocyclic lactone active agent, at least one IGR compound, and at least one anthelmintic compound, or pharmaceutically acceptable salts, hydrates or solvates thereof, together with a pharmaceutically acceptable carrier or diluent.

In one embodiment, the invention provides a composition that comprises a 1-arylpyrazole of formula (I) wherein R$_1$ is cyano, —C(O)R$_8$, —C(O)OR$_8$, —C(O)NR$_9$R$_{10}$, —C(=NOH)NH$_2$, —C(=NNH$_2$)R$_9$, or —C(S)NH$_2$, and all the other variables are as defined above.

In another embodiment, the invention provides a composition comprising a 1-arylpyrazole of formula (I) wherein R$_3$ is alkyl or haloalkyl.

In one embodiment, the invention provides a composition comprising a 1-arylpyrazole of formula (I) wherein:
R$_1$ is cyano, —C(O)R$_8$, —C(O)OR$_8$, —C(O)NR$_9$R$_{10}$, —C(=NOH)NH$_2$, —C(=NNH$_2$)R$_9$, or —C(S)NH$_2$; and
R$_2$ is —SCN, 4-5-dicyanoimidazol-2-yl, or —S(O)$_m$R$_{11}$.

In another embodiment, the invention provides a composition comprising a 1-arylpyrazole of formula (I) wherein:
R$_1$ is cyano, —C(O)R$_8$, —C(O)OR$_8$, —C(O)NR$_9$R$_{10}$, —C(=NOH)NH$_2$, —C(=NNH$_2$)R$_9$, or —C(S)NH$_2$;
R$_2$ is —SCN, 4-5-dicyanoimidazol-2-yl, or —S(O)$_m$R$_{11}$; and
R$_3$ is alkyl, haloalkyl or NR$_9$R$_{10}$.

In another embodiment, the invention provides a composition comprising a 1-arylpyrazole of formula (I) wherein:
R$_1$ is cyano;
R$_2$ is —SCN, 4-5-dicyanoimidazol-2-yl, or —S(O)$_m$R$_{11}$; and
R$_3$ is —N=C(R$_9$)(R$_{14}$), —N=C(R$_{10}$)—Z—(R$_9$), —N=C(R$_{10}$)—NR$_9$R$_{10}$, —N(R$_8$)—C(R$_{10}$)=NR$_9$.

In another embodiment, the invention provides a composition comprising a 1-arylpyrazole of formula (I) wherein:
R$_1$ is cyano;
R$_2$ is —SCN, 4-5-dicyanoimidazol-2-yl, or —S(O)$_m$R$_{11}$; and
R$_3$ is —N(R$_{11}$)C(O)CR$_{15}$R$_{10}$R$_{11}$, —N(R$_{11}$)C(O)aryl, —N(R$_{11}$)C(O)heteroaryl or —N(R$_{11}$)C(O)OR$_{10}$.

In still another embodiment, the invention provides a composition comprising a 1-arylpyrazole of formula (I) wherein:
R$_1$ is cyano;
R$_2$ is —SCN, 4-5-dicyanoimidazol-2-yl, or —S(O)$_m$R$_{11}$;
R$_3$ is alkyl, haloalkyl or NR$_9$R$_{10}$;
R$_4$, R$_5$ and R$_7$ are independently hydrogen, or halogen; and
X is C—R$_{13}$.

In another embodiment, the invention provides a composition comprising a 1-arylpyrazole of formula (I) wherein:
R$_1$ is cyano;
R$_2$ is —SCN, 4-5-dicyanoimidazol-2-yl, or —S(O)$_m$R$_{11}$;
R$_3$ is C$_1$-C$_4$alkyl or C$_1$-C$_4$haloalkyl;
R$_6$ is halogen, haloalkyl or SF$_5$; and
X is C—R$_{13}$.

In one embodiment, the invention provides a composition comprising a 1-arylpyrazole of formula (I) wherein:
R$_1$ is cyano;
R$_2$ is —S(O)$_m$R$_{11}$;
R$_3$ is C$_1$-C$_4$alkyl, C$_1$-C$_4$haloalkyl, or NR$_9$R$_{10}$;
R$_4$, R$_5$ and R$_7$ are independently hydrogen, or halogen;
R$_6$ is halogen, C$_1$-C$_4$alkyl, C$_1$-C$_4$haloalkyl, or SF$_5$;
X is C—R$_{13}$; and
R$_{13}$ is halogen or C$_1$-C$_4$haloalkyl.

In another embodiment, the invention provides a composition comprising a 1-arylpyrazole of formula (I) wherein:
R$_1$ is cyano;
R$_2$ is —S(O)$_m$R$_{11}$;
R$_3$ is —NH$_2$;
R$_4$, R$_5$ and R$_7$ are independently hydrogen, or halogen;
R$_6$ is C$_1$-C$_4$alkyl, C$_1$-C$_4$haloalkyl, or SF$_5$;
X is C—R$_{13}$; and
R$_{13}$ is hydrogen or halogen.

In yet another embodiment of the composition, a 1-arylpyrazole of formula (I) is provided wherein:
R$_1$ is cyano;
R$_2$ is —S(O)$_m$R$_{11}$;

$R_3$ is methyl, ethyl, propyl, or $C_1$-$C_4$haloalkyl;
$R_4$ is halogen;
$R_5$ and $R_2$ are hydrogen;
$R_6$ is $C_1$-$C_4$haloalkyl;
X is C—$R_{13}$;
$R_{11}$ is —$CF_3$, —$CClF_2$, or $CFCl_2$; and
$R_{13}$ is halogen.

In still another embodiment, the invention provides a composition comprising a 1-arylpyrazole of formula (I) wherein:
$R_1$ is cyano;
$R_2$ is —$S(O)_mR_{11}$;
$R_3$ is methyl or ethyl;
$R_4$ is chloro or fluoro;
$R_5$ and $R_2$ are hydrogen;
$R_6$ is —$CF_3$;
X is C—$R_{13}$;
$R_{11}$ is —$CFCl_2$ or $CF_3$; and
$R_{13}$ is chloro or fluoro.

In another embodiment, the invention provides a composition comprising a 1-aryl-alkyl or 5-haloalkylpyrazole of formula (IA) below:

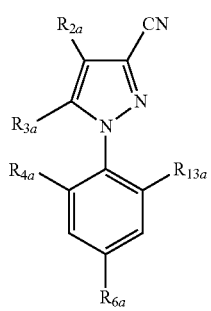

or a salt thereof, wherein:
$R_{2a}$ is —$S(O)_mR_{11a}$;
$R_{3a}$ is methyl, ethyl or $C_1$-$C_4$ haloalkyl;
$R_{4a}$ is halogen;
$R_{6a}$ is $C_1$-$C_4$alkyl or $C_1$-$C_4$haloalkyl;
$R_{13a}$ is halogen;
$R_{11a}$ is $C_1$-$C_4$ haloalkyl; and
m is 0, 1 or 2; or a pharmaceutically acceptable salt, hydrate or solvate thereof; in combination with at least one macrocyclic lactone active agent, at least one IGR compound, and at least one anthelmintic compound, or pharmaceutically acceptable salts, hydrates or solvates thereof, together with a pharmaceutically acceptable carrier or diluent.

Compounds of formula (IA) as well as process for the preparation of these compounds are described in US 2008/0031902 A1 and U.S. Pat. No. 7,759,381 to Lee et al., which are incorporated herein by reference in their entirety.

In another embodiment, the invention provides a composition that comprises a 1-aryl-5-alkyl pyrazole compound of formula (IA) wherein:
$R_{2a}$ is —$S(O)_mR_{11a}$;
$R_{3a}$ is methyl, or ethyl;
$R_{4a}$ is halogen;
$R_{6a}$ is $C_1$-$C_4$ haloalkyl;
$R_{13a}$ is halogen;
$R_{11a}$ is —$CF_3$, —$CClF_2$, or —$CFCl_2$; and
m is 0, 1 or 2.

In another embodiment, the invention provides a composition that comprises a 1-aryl-5-alkyl pyrazole compound of formula (IA) wherein:
$R_{2a}$ is —$S(O)_mR_{11a}$;
$R_{3a}$ is methyl, or ethyl;
$R_{4a}$ is halogen;
$R_{6a}$ is $C_1$-$C_4$ haloalkyl;
$R_{13a}$ is halogen;
$R_{11a}$ is —$CF_3$, —$CClF_2$, or —$CFCl_2$; and
m is 0, 1 or 2.

In still another embodiment of the invention, a composition is provided that comprises a 1-aryl-5-alkyl pyrazole compound of formula (IA) wherein:
$R_{2a}$ is —$S(O)_mR_{11a}$;
$R_{3a}$ is methyl;
$R_{4a}$ is —Cl;
$R_{6a}$ is —$CF_3$;
$R_{13a}$ is —F;
$R_{11a}$ is —$CFCl_2$ or $CF_3$; and
m is 0, 1 or 2.

In a preferred embodiment, the invention provides compositions for the treatment or prevention of a parasitic infection or infestation in an animal comprising at least one 1-arylpyrazole compound, at least one macrocyclic lactone active agent, at least one IGR, and at least one anthelmintic compound together with a pharmaceutically acceptable carrier, wherein the 1-arylpyrazole compound is 1-[2,6-dichloro-4-trifluoromethyl phenyl]-3-cyano-4-trifluoromethylsulfinyl-5-amino pyrazole, which is also known as fipronil.

The macrocyclic lactone compounds are also well known in the art and can be obtained commercially or through known synthesis techniques. For avermectins, ivermectin and abamectin, reference may be made, for example, to the publication "Ivermectin and Abamectin", 1989, by M. H. Fischer and H. Mrozik, William C. Campbell, published by Springer Verlag., "Macrocyclic Lactones in Antiparasitic Therapy", 2002, by J Vercruysse and R S Rew published by CABI Publishing or Albers-Schönberg et al. (1981), "Avermectins Structure Determination", *J. Am. Chem. Soc.*, 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", *Nat. Prod. Rep.*, 3, 87-121, Mrozik H. et al., 1983, Synthesis of Milbemycins from Avermectins, *Tetrahedron Lett.*, 24, 5333-5336, U.S. Pat. No. 4,134,973 and EP 0 677 054, all of which are incorporated herein by reference.

Macrocyclic lactones are either natural products or are semi-synthetic derivatives thereof. The structures of the avermectins and milbemycins are closely related, e.g., by sharing a complex 16-membered macrocyclic lactone ring; milbemycins lack the glycosidic moiety of the avermectins. The natural products avermectins are disclosed in U.S. Pat. No. 4,310, 519 to Albers-Schönberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950,360 as well as in the various references cited in "The Merck Index" 12th ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. No. 5,077, 308, U.S. Pat. No. 4,859,657, U.S. Pat. No. 4,963,582, U.S. Pat. No. 4,855,317, U.S. Pat. No. 4,871,719, U.S. Pat. No.

4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, U.S. Pat. No. 4,920,148 and EP 0 667 054, all incorporated herein by reference.

In a preferred embodiment, the compositions of the invention comprise at least one 1-arylpyrazole compound in combination with at least one avermectin or milbemycin compound, at least one IGR compound and at least one anthelmintic active agent. The avermectin and milbemycin active agents include, but are not limited to, abamectin, dimadectin, doramectin, emamectin, eprinomectin, ivermectin, latidectin, lepimectin, selamectin, milbemectin, milbemycin D, milbemycin oxime, moxidectin or nemadectin, or mixtures of these active agents.

The class of acaricides or insecticides known as insect growth regulators (IGRs) are well known in the art and represent a wide range of different chemical classes. IGR compounds are advantageously included in the compositions of the invention to provide superior efficacy against ectoparasites. These compounds all act by interfering with the development or growth of the insect pests. For example, some IGR compounds act by blocking the development of immature stages (eggs and larvae) into adult stages, or by inhibiting the synthesis of chitin. Some compounds in the IGR class mimic juvenile hormones. Insect growth regulators are described, for example, in U.S. Pat. No. 3,748,356; U.S. Pat. No. 3,818,047; U.S. Pat. No. 4,225,598; U.S. Pat. No. 4,798,837; U.S. Pat. No. 4,751,225, EP 0 179 022 or U.K. 2 140 010 as well as U.S. Pat. Nos. 6,096,329 and 6,685,954 (all incorporated herein by reference). Examples of IGRs suitable for use in the compositions of the invention include, but are not limited to, azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3-(2H)-one, cyromazine, chlorfluazuron, diflubenzuron, fluazuron, flucycloxuron, flufenoxuron, hexaflumuron, lufenuron, tebufenozide, teflubenzuron, triflumuron, novaluron, 1-(2,6-difluorobenzoyl)-3-(2-fluoro-4-trifluoromethyl)phenylurea, 1-(2,6-difluorobenzoyl)-3-(2-fluoro-4-trifluoromethyl)phenylurea, 1-(2,6-difluorobenzoyl)-3-(2-fluoro-4-(1,1,2,2-tetrafluoroethoxy) phenylurea and 1-(2,6-difluorobenzoyl)-3-(2-fluoro-4-trifluoromethyl)phenylurea.

In some preferred embodiments, the compositions of the invention comprise methoprene including (S)-methoprene, pyriproxyfens, hydroprene, cyromazine and lufenuron.

Various types of anthelmintic agents (in addition to one or more macrocyclic lactone) may be used in the compositions of the invention. In some embodiments, the compositions of the invention may include one or more antinematodal agents including, but not limited to, a benzimidazole, an imidazothiazole, a tetrahydropyrimidine, an organophosphate active agents, or mixtures of these active agents. In some embodiments, benzimidazoles including, but not limited to, thiabendazole, cambendazole, parbendazole, oxibendazole, mebendazole, flubendazole, fenbendazole, oxfendazole, albendazole, cyclobendazole, triclabendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel.

In still other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In certain embodiments, the anthelmintic agent in the compositions of the invention can be a biologically active peptide or protein including, but not limited to, depsipeptides, which act at the neuromuscular junction by stimulating presynaptic receptors belonging to the secretin receptor family resulting in the paralysis and death of parasites. In one particular embodiment of the depsipeptide, the depsipeptide is emodepside (see Willson et al., *Parasitology*, January 2003, 126(Pt 1):79-86).

In another embodiment of the invention, nodulisporic acid and its derivatives (a class of known acaricidal, anthelmintic, anti-parasitic and insecticidal agents) may be included in the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be included in the compositions of the invention. These compounds are described, for example, in WO 2004/024704; Sager et al., *Veterinary Parasitology*, 2009, 159, 49-54; Kaminsky et al., *Nature vol.* 452, 13 Mar. 2008, 176-181. The compositions of the invention may also include aryloazol-2-yl cyanoethylamino compounds such as those described in US 2008/0312272 to Soll et al. and those described in U.S. patent application Ser. No. 12/618,308, and thioamide derivatives of these compounds, as described in U.S. patent application Ser. No. 12/582,486, filed Oct. 20, 2009, all of which are incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the para-herquamide derivatives can be found, for example, in WO 91/09961, WO 92/22555, WO 97/03988, WO 01/076370, WO 09/004,432, U.S. Pat. No. 5,703,078 and U.S. Pat. No. 5,750,695, all of which are hereby incorporated by reference in their entirety.

In another embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In one embodiment, the invention provides a composition comprising at least one 1-arylpyrazole of formula (I) or (IA) in combination with at least one avermectin or milbemycin active agent, at least one IGR compound, and at least one of a benzimidazole anthelmintic, an imidazothiazole anthelmintic, a tetrahydropyrimidine anthelmintic, levamisole, pyrantel or praziquantel, in combination with a pharmaceutically acceptable carrier or diluent.

In another embodiment, the invention provides a composition comprising at least one 1-arylpyrazole of formula (I) or (IA) in combination with at least one of abamectin, dimadectin, doramectin, emamectin, eprinomectin, ivermectin, latidectin, lepimectin, selamectin, milbemectin, milbemycin D, milbemycin oxime, moxidectin or nemadectin; at least one IGR compound, and at least one of a benzimidazole anthelmintic, imidazothiazole anthelmintic, tetrahydropyrimidine anthelmintic, levamisole, pyrantel or praziquantel, in combination with a pharmaceutically acceptable carrier or diluent.

In another embodiment, the invention provides a composition comprising at least one 1-arylpyrazole of formula (I) or (IA) in combination with at least one of abamectin, dimadectin, doramectin, emamectin, eprinomectin, ivermectin, latidectin, lepimectin, selamectin, milbemectin, milbemycin D, milbemycin oxime, moxidectin or nemadectin; at least one of methoprene, pyriproxyfen, hydroprene, cyromazine, fluazuron, lufenuron, novaluron, 1-(2,6-difluorobenzoyl)-3-(2-fluoro-4-(trifluoromethyl)phenylurea, or novaluron; and at least one of a benzimidazole anthelmintic, imidazothiazole anthelmintic, tetrahydropyrimidine anthelmintic, levamisole, pyrantel or praziquantel, in combination with a pharmaceutically acceptable carrier or diluent.

In another embodiment, the invention provides a composition comprising at least one 1-arylpyrazole of formula (I):

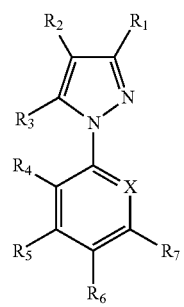

(I)

wherein $R_1$ is cyano;

$R_2$ is —SCN, 4-5-dicyanoimidazol-2-yl, or —S(O)$_m$R$_{11}$;

$R_3$ is alkyl, haloalkyl or NR$_9$R$_{10}$;

$R_4$, $R_5$ and $R_2$ are independently hydrogen, or halogen; and

X is C—$R_{13}$; and $R_6$, $R_9$, $R_{10}$, $R_{11}$, $R_{13}$ and m are as defined above for formula (I); in combination with at least one of abamectin, dimadectin, doramectin, emamectin, eprinomectin, ivermectin, latidectin, lepimectin, selamectin, milbemectin, milbemycin D, milbemycin oxime, moxidectin or nemadectin; at least one IGR compound, and at least one anthelmintic compound; in combination with a pharmaceutically acceptable carrier or diluent.

In another embodiment, the invention provides a composition comprising at least one 1-arylpyrazole of formula (I):

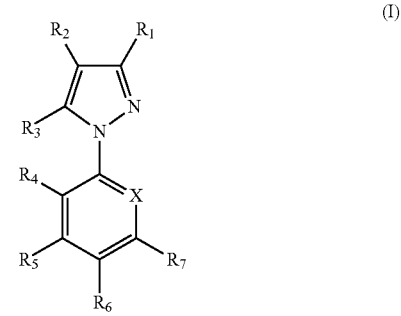

(I)

wherein $R_1$ is cyano;

$R_2$ is —SCN, 4-5-dicyanoimidazol-2-yl, or —S(O)$_m$R$_{11}$;

$R_3$ is alkyl, haloalkyl or NR$_9$R$_{10}$;

$R_4$, $R_5$ and $R_2$ are independently hydrogen, or halogen; and

X is C—$R_{13}$; and $R_6$, $R_9$, $R_{10}$, $R_{11}$, $R_{13}$ and m are as defined above for formula (I); in combination with at least one of abamectin, dimadectin, doramectin, emamectin, eprinomectin, ivermectin, latidectin, lepimectin, selamectin, milbemectin, milbemycin D, milbemycin oxime, moxidectin or nemadectin; at least one of azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3-(2H)-one, cyromazine, chlorfluazuron, diflubenzuron, fluazuron, flucycloxuron, flufenoxuron, hexaflumuron, lufenuron, tebufenozide, teflubenzuron, triflumuron, novaluron, 1-(2,6-difluorobenzoyl)-3-(2-fluoro-4-trifluoromethyl)phenylurea, 1-(2,6-difluorobenzoyl)-3-(2-fluoro-4-trifluoromethyl)phenylurea, 1-(2,6-difluorobenzoyl)-3-(2-fluoro-4-(1,1,2,2-tetrafluoroethoxy)phenylurea or 1-(2,6-difluorobenzoyl)-3-(2-fluoro-4-trifluoromethyl)phenylurea; and at least one anthelmintic compound; in combination with a pharmaceutically acceptable carrier or diluent.

In yet another embodiment, the invention provides a composition comprising at least one 1-arylpyrazole of formula (I):

(I)

wherein
$R_1$ is cyano;
$R_2$ is —SCN, 4-5-dicyanoimidazol-2-yl, or —S(O)$_m$R$_{11}$;
$R_3$ is alkyl, haloalkyl or NR$_9$R$_{10}$;
$R_4$, $R_5$ and $R_2$ are independently hydrogen, or halogen; and X is C—R$_{13}$; and R$_6$, R$_9$, R$_{10}$, R$_{11}$, R$_{13}$ and m are as defined above for formula (I); in combination with at least one of abamectin, dimadectin, doramectin, emamectin, eprinomectin, ivermectin, latidectin, lepimectin, selamectin, milbemectin, milbemycin D, milbemycin oxime, moxidectin or nemadectin; at least one of azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3-(2H)-one, cyromazine, chlorfluazuron, diflubenzuron, fluazuron, flucycloxuron, flufenoxuron, hexaflumuron, lufenuron, tebufenozide, teflubenzuron, triflumuron, novaluron, 1-(2,6-difluorobenzoyl)-3-(2-fluoro-4-trifluoromethyl)phenylurea, 1-(2,6-difluorobenzoyl)-3-(2-fluoro-4-trifluoromethyl)phenylurea, 1-(2,6-difluorobenzoyl)-3-(2-fluoro-4-(1,1,2,2-tetrafluoroethoxy)phenylurea or 1-(2,6-difluorobenzoyl)-3-(2-fluoro-4-trifluoromethyl)phenylurea; and at least one of a benzimidazole anthelmintic, an imidazothiazole anthelmintic, a tetrahydropyrimidine anthelmintic, phenothiazine, piperazine, dialkylcarbamazine, an ethanolamine, miracil, praziquantel, a nodulisporic acid derivative, an amino acetonitrile anthelmintic, an aryloazol-2-yl cyanoethylamino anthelmintic, an isoxazoline active agent or a paraherquamide anthelmintic; in combination with a pharmaceutically acceptable carrier or diluent.

In yet another embodiment, the invention provides a composition comprising at least one 1-arylpyrazole of formula (I):

(I)

wherein
$R_1$ is cyano;
$R_2$ is —SCN, 4-5-dicyanoimidazol-2-yl, or —S(O)$_m$R$_{11}$;
$R_3$ is alkyl, haloalkyl or NR$_9$R$_{10}$;
$R_4$, $R_5$ and $R_2$ are independently hydrogen, or halogen; and X is C—R$_{13}$; and R$_6$, R$_9$, R$_{10}$, R$_{11}$, R$_{13}$ and m are as defined above for formula (I); in combination with at least one of abamectin, dimadectin, doramectin, emamectin, eprinomectin, ivermectin, latidectin, lepimectin, selamectin, milbemectin, milbemycin D, milbemycin oxime, moxidectin or nemadectin; at least one of azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3-(2H)-one, cyromazine, chlorfluazuron, diflubenzuron, fluazuron, flucycloxuron, flufenoxuron, hexaflumuron, lufenuron, tebufenozide, teflubenzuron, triflumuron, novaluron, 1-(2,6-difluorobenzoyl)-3-(2-fluoro-4-trifluoromethyl)phenylurea, 1-(2,6-difluorobenzoyl)-3-(2-fluoro-4-trifluoromethyl)phenylurea, 1-(2,6-difluorobenzoyl)-3-(2-fluoro-4-(1,1,2,2-tetrafluoroethoxy)phenylurea or 1-(2,6-difluorobenzoyl)-3-(2-fluoro-4-trifluoromethyl)phenylurea; and at least one of thiabendazole, cambendazole, parbendazole, oxibendazole, mebendazole, flubendazole, fenbendazole, oxfendazole, albendazole, cyclobendazole, triclabendazole, febantel, thiophanate and its o,o-dimethyl analogue, tetramisole, levamisole, butamisole, pyrantel, oxantel, morantel, disophenol, bephenium, thenium closylate, methyridine, pyrvinium chloride, pyrvinium pamoate, dithiazanine iodide, bitoscanate, suramin sodium, phthalofyne, miracil D, mirasan, praziquantel, clonazepam and its 3-methyl derivative, oltipraz, lucanthone, hycanthone, oxamniquine, amoscanate, niridazole, nitroxynil, hexachlorophene, bithionol, bithionol sulfoxide, menichlopholan, tribromsalan, oxyclozanide, clioxanide, rafoxanide, brotianide, bromoxanide, and closantel, triclabendazole, diamfenetide, clorsulon, hetolin, emetine, arecoline, bunamidine, niclosamide, nitroscanate, paromomycin, paromomycin II, a depsipeptide such as emodepside, an amino acetonitrile such as monepantel, an aryloazol-2-yl cyanoethylamino compound such as N-[2-(6-bromo-2H-pyrazolo[4,3-b]pyridin-2-yl)-2-cyano-2-methylethyl]-4-trifluoromethoxybenzamide, a paraherquamide such as derquantel, or marcfortine A, B or C; in combination with a pharmaceutically acceptable carrier or diluent.

In yet another embodiment, the invention provides a composition comprising at least one 1-arylpyrazole of formula (I):

(I)

wherein
$R_1$ is cyano;
$R_2$ is —S(O)$_m$R$_{11}$;
$R_3$ is NR$_9$R$_{10}$;
$R_4$, $R_5$ and $R_7$ are independently hydrogen, or halogen; and X is C—R$_{13}$; and R$_6$, R$_9$, R$_{10}$, R$_{11}$, R$_{13}$ and m are as defined above for formula (I); in combination with at least one of eprinomectin, ivermectin, selamectin, milbemectin, milbemycin D, milbemycin oxime, or moxidectin; at least one of (S)-methoprene, pyriproxyfen, hydroprene, cyromazine, fluazuron, lufenuron, or novaluron; and at least one of a at least one of a benzimidazole anthelmintic, an imidazothiazole anthelmintic, a tetrahydropyrimidine anthelmintic, phenothiazine, piperazine, dialkylcarbamazine, a ethanolamine, miracil, praziquantel, a nodulisporic acid derivative, an amino acetonitrile anthelmintic, an aryloazol-2-yl cyanoethylamino anthelmintic, an isoxazoline active agent or a paraherquamide anthelmintic; in combination with a pharmaceutically acceptable carrier or diluent.

In yet another embodiment, the invention provides a composition comprising at least one 1-arylpyrazole of formula (I):

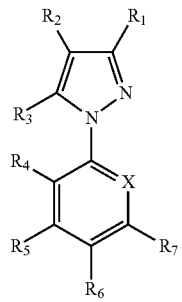

wherein
$R_1$ is cyano;
$R_2$ is —$S(O)_m R_{11}$;
$R_3$ is $NR_9 R_{10}$;
$R_4$, $R_5$ and $R_2$ are independently hydrogen, or halogen;
$R_6$ is $C_1$-$C_4$haloalkyl, or $SF_5$;
X is C—$R_{13}$;
$R_{11}$ is $C_1$-$C_4$alkyl or $C_1$-$C_4$haloalkyl;

$R_{13}$ is halogen; and $R_9$ and $R_{10}$ and m are as defined above for formula (I); in combination with at least one of eprinomectin, ivermectin, selamectin, milbemectin, milbemycin D, milbemycin oxime, or moxidectin; at least one of (S)-methoprene, pyriproxyfen, hydroprene, cyromazine, fluazuron, lufenuron, or novaluron; and at least one of thiabendazole, cambendazole, parbendazole, oxibendazole, mebendazole, flubendazole, fenbendazole, oxfendazole, albendazole, cyclobendazole, triclabendazole, febantel, tetramisole, levamisole, pyrantel, morantel, praziquantel, closantel, triclabendazole, clorsulon, emodepside, amino acetonitriles such as monepantel, an aryloazol-2-yl cyanoethylamino compound such as N-[2-(6-bromo-2H-pyrazolo[4,3-b]pyridin-2-yl)-2-cyano-2-methylethyl]-4-trifluoromethoxybenzamide, or a paraherquamide such as derquantel; in combination with a pharmaceutically acceptable carrier or diluent.

In yet another embodiment, the invention provides a composition comprising at least one 1-arylpyrazole of formula (I):

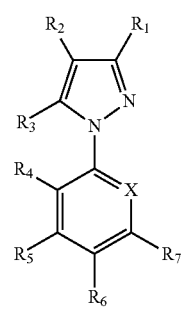

wherein
$R_1$ is cyano;
$R_2$ is —$S(O)_m R_{11}$;
$R_3$ is $NR_9 R_{10}$;
$R_4$, $R_5$ and $R_2$ are independently hydrogen, or halogen;
$R_6$ is $C_1$-$C_4$haloalkyl, or $SF_5$;
X is C—$R_{13}$;
$R_{11}$ is $C_1$-$C_4$alkyl or $C_1$-$C_4$haloalkyl;
$R_{13}$ is halogen; and $R_9$ and $R_{10}$ and m are as defined above for formula (I); in combination with at least one of eprinomectin, ivermectin, selamectin, milbemectin, milbemycin D, milbemycin oxime, or moxidectin; at least one of (S)-methoprene, pyriproxyfen, hydroprene, cyromazine, fluazuron, lufenuron, or novaluron; and at least one of thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile such as monepantel, or an aryloazol-2-yl cyanoethylamino compound such as N-[2-(6-bromo-2H-pyrazolo[4,3-b]pyridin-2-yl)-2-cyano-2-methylethyl]-4-trifluoromethoxybenzamide; in combination with a pharmaceutically acceptable carrier or diluent.

In yet another embodiment, the invention provides a composition comprising at least one 1-arylpyrazole of formula (I):

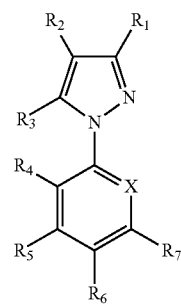

wherein
$R_1$ is cyano;
$R_2$ is —$S(O)_m R_{11}$;
$R_3$ is $NR_9 R_{10}$;
$R_4$, $R_5$ and $R_2$ are independently hydrogen, or halogen;
$R_6$ is $C_1$-$C_4$haloalkyl, or $SF_5$;
X is C—$R_{13}$;
$R_{11}$ is $C_1$-$C_4$alkyl or $C_1$-$C_4$haloalkyl;
$R_{13}$ is halogen; and $R_9$ and $R_{10}$ and m are as defined above for formula (I); in combination with at least one of eprinomectin, ivermectin, milbemycin oxime, or moxidectin; at least one of (S)-methoprene, pyriproxyfen, or lufenuron; and at least one of febantel, levamisole, pyrantel, or praziquantel; in combination with a pharmaceutically acceptable carrier or diluent.

In another embodiment, the invention provides a composition comprising a 1-aryl-alkyl or 5-haloalkylpyrazole of formula (IA) below:

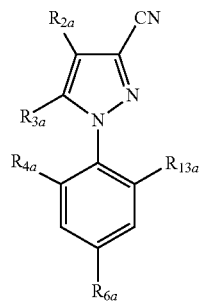

(IA)

or a salt thereof, wherein:
$R_{2a}$ is —S(O)$_m R_{11a}$;
$R_{3a}$ is methyl, ethyl or $C_1$-$C_4$ haloalkyl;
$R_{4a}$ is halogen;
$R_{6a}$ is $C_1$-$C_4$ alkyl or haloalkyl;
$R_{13a}$ is halogen;
$R_{11a}$ is $C_1$-$C_4$ haloalkyl; and
m is 0, 1 or 2; in combination with at least one of eprinomectin, ivermectin, selamectin, milbemectin, milbemycin D, milbemycin oxime, or moxidectin; at least one of (S)-methoprene, pyriproxyfen, hydroprene, cyromazine, fluazuron, lufenuron, or novaluron; and at least one of thiabendazole, oxibendazole, mebendazole, fenbendazole, oxfendazole, albendazole, triclabendazole, febantel, levamisole, pyrantel, morantel, praziquantel, closantel, clorsulon, amino acetonitrile such as monepantel, aryloazol-2-yl cyanoethylamino compound such as N-[2-(6-bromo-2H-pyrazolo[4,3-b]pyridin-2-yl)-2-cyano-2-methylethyl]-4-trifluoromethoxybenzamide; in combination with a pharmaceutically acceptable carrier or diluent.

In another embodiment, the invention provides a composition comprising a 1-aryl-alkyl or 5-haloalkylpyrazole of formula (IA) below:

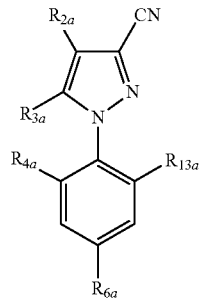

(IA)

or a salt thereof, wherein:
$R_{2a}$ is —S(O)$_m R_{11a}$;
$R_{3a}$ is methyl, or ethyl;
$R_{4a}$ is halogen;
$R_{6a}$ is $C_1$-$C_4$ haloalkyl;
$R_{13a}$ is halogen;
$R_{11a}$ is —CF$_3$, —CClF$_2$, or —CFCl$_2$; and
m is 0, 1 or 2; in combination with at least one of eprinomectin, ivermectin, milbemycin oxime or moxidectin; at least one of (S)-methoprene, pyriproxyfen, or lufenuron; and at least one of febantel, levamisole, pyrantel, or praziquantel; in combination with a pharmaceutically acceptable carrier or diluent.

In another embodiment, the invention provides a composition comprising a 1-aryl-alkyl or 5-haloalkylpyrazole of formula (IA) below:

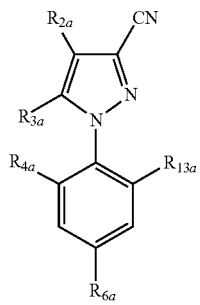

(IA)

or a salt thereof, wherein:
$R_{2a}$ is —S(O)$_m R_{11a}$;
$R_{3a}$ is methyl;
$R_{4a}$ is —Cl;
$R_{6a}$ is —CF$_3$;
$R_{13a}$ is —F;
$R_{11a}$ is —CFCl$_2$ or CF$_3$; and
m is 0, 1 or 2; in combination with at least one of eprinomectin, ivermectin, milbemycin oxime, or moxidectin; at least one of (S)-methoprene, pyriproxyfen, or lufenuron; and at least one of febantel, levamisole, pyrantel, or praziquantel; in combination with a pharmaceutically acceptable carrier or diluent.

In preferred embodiment, the invention provides a composition comprising 5-amino-3-cyano-1-(2,6-dichloro-4-trifluoromethylphenyl)-4-trifluoromethylsulfinylpyrazole (fipronil) in combination with at least one of eprinomectin, ivermectin, selamectin, milbemectin, milbemycin D, milbemycin oxime or moxidectin; at least one of (S)-methoprene, pyriproxyfen, hydroprene, cyromazine, fluazuron, lufenuron, or novaluron; and at least one of thiabendazole, oxibendazole, mebendazole, fenbendazole, oxfendazole, albendazole, triclabendazole, febantel, levamisole, pyrantel, morantel, praziquantel, closantel, clorsulon, amino acetonitrile such as monepantel, aryloazol-2-yl cyanoethylamino compound such as N-[2-(6-bromo-2H-pyrazolo[4,3-b]pyridin-2-yl)-2-cyano-2-methylethyl]-4-trifluoromethoxybenzamide; in combination with a pharmaceutically acceptable carrier or diluent.

In another preferred embodiment, the invention provides a composition comprising 5-amino-3-cyano-1-(2,6-dichloro-4-trifluoromethylphenyl)-4-trifluoromethylsulfinylpyrazole (fipronil) in combination with at least one of eprinomectin, ivermectin, milbemycin oxime or moxidectin; at least one of (S)-methoprene, pyriproxyfen, hydroprene, cyromazine, fluazuron, lufenuron, or novaluron; and at least one of a albendazole, triclabendazole, levamisole, pyrantel or praziquantel; in combination with a pharmaceutically acceptable carrier or diluent.

In yet another preferred embodiment, the invention provides a formulation comprising 5-amino-3-cyano-1-(2,6-dichloro-4-trifluoromethylphenyl)-4-trifluoromethylsulfinylpyrazole (fipronil) in combination with at least one of eprinomectin, ivermectin, milbemycin oxime or moxidectin; at least one of (S)-methoprene, pyriproxyfen, lufenuron, or novaluron; and at least one of a levamisole, febantel, pyrantel or praziquantel; in combination with a pharmaceutically acceptable carrier or diluent.

In another preferred embodiment, the invention provides a composition comprising 5-amino-3-cyano-1-(2,6-dichloro-4-trifluoromethylphenyl)-4-trifluoromethylsulfinylpyrazole (fipronil) in combination with at least one of eprinomectin, ivermectin, milbemycin oxime or moxidectin; (S)-methoprene; and at least one of febantel, pyrantel or praziquantel; in combination with a pharmaceutically acceptable carrier or diluent.

In yet another preferred embodiment, the invention provides a composition comprising 5-amino-3-cyano-1-(2,6-dichloro-4-trifluoromethylphenyl)-4-trifluoromethylsulfinylpyrazole (fipronil) in combination with at least one of eprinomectin ivermectin, or milbemycin oxime; (S)-methoprene; and praziquantel; in combination with a pharmaceutically acceptable carrier or diluent.

The compositions of the invention, which include at least four different active agents in a carrier system that is compatible with each active agent, have been surprisingly discovered to be stable and effective against a broad spectrum of ectoparasites and endoparasites. It will be well apparent to one of skill in the art that combination of multiple active agents in a single composition without affecting the stability of the active agents during storage or the efficacy of each active upon administration is extremely difficult and unpredictable. The four classes of active agents included in the inventive compositions have substantially different structures and consequently have different solubility and stability requirements. This presents a significant problem when including the multiple active agents in a single formulation, particularly in formulations that require the four active agents to be in solution, such as in spot-on or pour-on formulations. The solubility, log P, molecular weight and other physical characteristics of each active agent in the carrier system affects the ability to deliver the drug into the coat of the animal or to permeate the skin as required. The identification of a suitable carrier system that will solubilize each active agent in a stable solution while being able to deliver the active agents to the targeted location on the animal at the required concentration is a very difficult task and is not predictable or obvious.

Furthermore, the identification of a suitable carrier system to produce a stable composition comprising four different classes of active agents is challenging and unobvious.

It is well known in the art that it is very difficult to formulate macrocyclic lactone active agents together with certain other actives due to different carrier requirements and the susceptibility of macrocyclic lactones to degrade in certain solvents. Avermectins and milbemycins are poorly soluble in water and not compatible with acidic conditions, while some anthelmintic agents such as levamisole are more water soluble and require acidic pH for optimum stability (see US 2006/0128641 A1). For example, WO 00/74489 describes liquid compositions comprising a macrocyclic lactone and another anthelmintic (levamisole) where the composition contains separate phases which contain the different active agents in order to meet the different solubility and stability requirements of each active. U.S. Pat. No. 6,489,303 to Jancys et al. describes that mixtures of a macrocyclic lactone and another insoluble anthelmintic agent resulted in an increased rate of degradation of the macrocyclic lactone active agent, requiring the addition of excess antioxidant to stabilize the mixture. Therefore, the combination of four active agents, including a macrocyclic lactone, in a single liquid composition that is both stable for an extended period of time and efficacious against a broad spectrum of ectoparasites and endoparasites represents a significant achievement in the field of veterinary medicine that is not predictable or obvious.

The compositions of the present invention combine active agents that are efficacious against both internal and external parasites. For example, 1-arylpyrazoles and IGR compounds such as fipronil and methoprene are active against fleas and ticks on the haircoat of the animal where fleas and ticks come in contact with the compounds. In contrast, macrocyclic lactones and anthelmintic compounds exert their activity against internal parasites such as parasitic worms by systemic exposure. Because the carrier vehicle in the composition has a crucial impact on the distribution of active agents in the animal, it is extremely problematic to attain a formulation comprising a combination of active agents that require either systemic or topical exposure to achieve the desired efficacy against both internal and external parasites in one liquid carrier system. Thus, the compositions of the invention, which in some embodiments are in the form of topical solutions in a homogeneous carrier, are unique in that they achieve excellent long-lasting efficacy against external parasites such as fleas and ticks while at the same time effectively controlling internal parasites such as *Dirofilaria immitis* (heartworm), roundworms and other parasitic worms. The compositions of the invention surprisingly achieve the required distribution of an effective amount each different active to the site of the animal required to achieve the superb efficacy against harmful internal and external parasites demonstrated in the examples. In particular, the superb efficacy achieved against *Dirofilaria immitis* (heartworm), roundworms including *T. cati*, tapeworms including *D. caninum*, and hookworms including *A. tubaeforme* concurrently with the long-lasting efficacy achieved against fleas and ticks is noteworthy and unique.

It is well know that macrocyclic lactone actives and anthelmintic active agents are required to be absorbed into the blood stream to be efficacious against internal parasites. As such, formulations directed to the treatment and control of endoparasites typically contain strong solvents and/or penetration enhancing agents that can disrupt the barrier function of the stratum corneum to allow passage of the actives into the blood stream. Examples of solvents with this property include dimethylsulfoxide and dimethyl isosorbide, among others. Penetration enhancers include compounds with a polar head group and long alkyl chains such as non-ionic surfactants, oleic acid, decyl methyl sulphoxide and Azone, among others.

However, this approach is not suitable for use with active agents such as 1-arylpyrazole or IGR actives that must be present in effective concentrations at the surface (haircoat) of the animal to be effective against ectoparasites such as fleas and ticks, as excessive passage of these active into the blood stream would decrease the efficacy against ectoparasites that are present on the surface of the animal. Additionally, it is well known that high concentrations of certain arylpyrazoles in the blood stream may result in adverse effects. Thus, the use of solvents or penetration enhancers that are suitable for driving sufficient concentrations of macrocyclic lactone and anthelmintic active agents into the blood stream by disrupting the barrier function of the stratum corneum would not expected to be suitable for formulations comprising actives that are required to be maintained at the surface of the animal.

It was surprisingly found that the topical compositions of the present invention are able to achieve both effective transdermal penetration of the macrocyclic lactone and anthelmintic active agents while maintaining effective amounts of the 1-arylpyrazole and IGR active agents on the surface of the animal. This result is unexpected, as the use of solvents that are known to function as penetration enhancers would be expected to also carry high proportions of the 1-arylpyrazole and IGR active agents into the systemic circulation rather than maintaining effective concentrations of the ectoparasiticide on the surface of the animal. By achieving effective concentrations of each active at the required site on the animal, the compositions of the invention are able to effectively control both endoparasites and ectoparasites.

In a preferred embodiment of the inventive compositions, the composition will be in the form of a liquid solution or suspension. The pharmaceutically acceptable carrier may be any suitable carrier or diluent commonly used in the formulation art including aqueous or organic solvents or mixtures of solvents. These organic solvents may be found, for example, in Remington Pharmaceutical Sciences, 16$^{th}$ Edition (1986). Organic solvents that can be used in the invention include those described above, and include but are not limited to: acetyltributyl citrate, oleic acid, fatty acid esters such as the dimethyl ester, diisobutyl adipate, diisopropyl adipate (also known as CERAPHYL 230), ketones including acetone, methylisobutyl ketone (MIK) and methyl ethyl ketone and the like, acetonitrile, benzyl alcohol, methanol, ethyl alcohol, isopropanol, butanol, aromatic ethers such as anisole, butyl diglycol, amides including dimethylacetamide and dimethylformamide, dimethyl sulfoxide, ethylene glycol, propylene glycol, glycol ethers including propylene glycol monomethyl ether, propylene glycol monoethyl ether, dipropylene glycol n-butyl ether, ethylene glycol monoethyl ether, ethylene glycol monomethyl ether, diethylene glycol monoethyl ether, glycol carbonates, monomethylacetamide, dipropylene glycol monomethyl ether, liquid polyoxyethylene glycols (PEG) of different average molecular weight ranges, 2-pyrrolidone including N-methylpyrrolidone, glycerol formal, dimethyl isosorbide, triacetin, $C_1$-$C_{10}$ esters of carboxylic acids such as butyl or octyl acetate, benzyl acetate, aryl esters including benzyl benzoate, ethyl benzoate and the like, propylene carbonate, butylene carbonate, and diethyl phthalate, or a mixture of at least two of these solvents.

These solvents can be supplemented by various excipients according to the nature of the desired phases, such as $C_8$-$C_{10}$ caprylic/capric triglyceride (ESTASAN or MIGLYOL 812), oleic acid or propylene glycol.

In one embodiment of the invention, the pharmaceutically acceptable carrier of the formulation comprises $C_1$-$C_{10}$ alcohols or esters thereof (including acetates, such as ethyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, or mixtures thereof.

In some preferred embodiments, the carrier or diluent is a derivative of glycerol including, but not limited to, glycerol monoesters (e.g. monoglycerides), glycerol diesters (e.g. diglycerides), glycerol triesters (e.g. triglycerides such as triacetin), or glycerol formal, or mixtures thereof. Glycerol formal is a mixture of 5-hydroxy-1,3-dioxane and 4-hydroxymethyl-1,3-dioxolane (approximately 60:40), which are cyclic ether compounds derived from glycerol and having 2 oxygen atoms in the ring structure and substituted by alcohol group. Glycerol Formal is a low odor and low toxic solvent for a wide variety of applications in pharmaceutical and cosmetics industry including anti-parasite veterinary formulations.

In another embodiment of the invention, the organic solvents may comprise diisopropyl adipate, dipropylene glycol monomethyl ether, propylene glycol monomethyl ether, 2-pyrrolidone including N-methylpyrrolidone, diethylene glycol monoethyl ether, triacetin, butyl acetate, octyl acetate, propylene carbonate, oleic acid, or a mixture of at least two of these solvents.

In one embodiment, preferred solvents include $C_1$-$C_{10}$ esters of carboxylic acids such as butyl or octyl acetate.

In some embodiments of the invention, the carrier comprises dimethyl isosorbide. Dimethyl Isosorbide (DMI) is a high purity solvent and carrier which offers a safe, effective delivery enhancement mechanism for active ingredients in personal care products and pharmaceutical formulations. In addition dimethyl isosorbide is sometimes used as an epidermal penetration enhancer to provide enhanced penetration of active agents to the epidermis. It may also provide delivery of active agents into the skin while avoiding crystallization of the active agent, which will severely limit the effectiveness of the formulation. Dimethyl Isosorbide is soluble in a variety of ingredients including water, cottonseed oil, isopropanol, isopropyl myristate, propylene glycol, polysorbate 20, and polysorbate 80. It is insoluble in hydrogenated castor oil, lanolin, mineral oils or silicone oil (dimethicone).

In other embodiments, the carrier or diluent can be dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides, or mixtures thereof.

The compositions of the invention can be in a variety of forms suitable for different forms of administration including, but are not limited to, oral formulations, injectable formulations, and topical, dermal or subdermal formulations.

In some embodiments the compositions of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874, which are incorporated herein by reference in their entirety, to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides. In another embodiment of the oily phase, the triglycerides are medium-chain triglycerides, for example $C_8$-$C_{10}$ caprylic/capric triglyceride. Another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid or other known preservatives.

Aqueous suspensions may contain the active agents in admixture with excipients suitable for the manufacture of aqueous suspensions. Such excipients are suspending agents, for example, sodium carboxymethylcellulose, methylcellulose, hydroxy-propylmethylcellulose, sodium alginate, polyinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889, both of which are incorporated herein by reference. In addition to the active agent of the invention, the paste can also contain fumed silica; a viscosity modifier; a carrier; optionally, an absorbent; and optionally, a colorant, stabilizer, surfactant, or preservative.

In one embodiment, the process for preparing a paste formulation comprises the steps of:

(a) dissolving or dispersing the active agent into the carrier by mixing;

(b) adding the fumed silica to the carrier containing the dissolved active agent compound and mixing until the silica is dispersed in the carrier;

(c) allowing the intermediate formed in (b) to settle for a time sufficient in order to allow the air entrapped during step (b) to escape; and (d) adding the viscosity modifier to the intermediate with mixing to produce a uniform paste.

The above steps are illustrative, but not limiting. For example, step (a) can be the last step.

In one embodiment of the formulation, the formulation is a paste containing the active agent compound, fumed silica, a viscosity modifier, an absorbent, a colorant; and a hydrophilic carrier which is a triacetin, a monoglyceride, a diglyceride, or a triglyceride. The paste may also include a viscosity modifier including, but is not limited to, PEG 200, PEG 300, PEG 400, PEG 600, monoethanolamine, triethanolamine, glycerol, propylene glycol, polyoxyethylene (20) sorbitan mono-oleate (polysorbate 80 or Tween 80), or polyoxamers (e.g., Pluronic L 81); an absorbent including, but not limited to, magnesium carbonate, calcium carbonate, starch, or cellulose and its derivatives.

Colorants may be added to the inventive formulations. Colorants contemplated by the present invention are those commonly known in the art. Specific colorants include, for example, dyes, FD&C Blue #1 Aluminum Lake, caramel, colorant based upon iron oxide or a mixture of any of the foregoing. Especially preferred are organic dyes and titanium dioxide. Preferred ranges include from about 0.5% to about 25%.

In some embodiments of the invention, the compositions may be in the form of a sterile injectable solutions or aqueous or oleagenous suspensions. These suspensions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In a preferred embodiment of the invention, compositions suitable for topical administration to an animal are provided. Topical, dermal and subdermal formulations can include emulsions, creams, ointments, gels, pastes, powders, shampoos, pour-on formulations, ready-to-use formulations, spot-on solutions and suspensions. Topical application of the inventive compositions can allow for the active agents to be delivered and distributed through the sebaceous glands of the animal or throughout the haircoat and/or allow some active agents to achieve a systemic effect (plasma concentration). When the compound is distributed throughout sebaceous glands, the sebaceous glands can act as a reservoir, whereby there can be a long-lasting, e.g. 1-2 months effect or longer. Cotchet and co-workers reported the distribution of fipronil, a 1-arylpyrazole compound, to the stratum corneum, the viable epidermis and the sebaceous glands and epithelial layers of beagle dogs after spot-on administration (see Cochet et al., Eur. J. Drug Metab. Pharmacokinet . . . , 1997, 22(3), 211-216). Using $^{14}C$ radiolabeled drug, the publication demonstrated that fipronil is displaced from the point of application and distributed to the whole skin, where it was persistently detected for up to 56 days after treatment.

In preferred embodiment, the compositions of the invention are in the form of a spot-on formulation that is applied to a localized area on an animal, rather than the entire coat of the animal or a large portion of the animal's coat. In one embodiment of a localized region, the location is between the shoulders. The spot-on formulation according to the present invention provide long-lasting and broad-spectrum efficacy against ectoparasites and endoparasites when the solution is applied to the mammal or bird. The spot-on formulations provide for topical administration of a concentrated solution, suspension, microemulsion or emulsion for intermittent application to a spot on the animal, generally between the two shoulders (solution of spot-on type).

Spot-on formulations are well known techniques for topically delivering an antiparasitic agent to a limited area of the host. For example, U.S. Pat. Nos. 5,045,536 6,426,333; 6,482,425; 6,962,713; and 6,998,131, all incorporated herein by reference, describe spot-on formulations. WO 01/957715, also incorporated herein by reference, describes a method for controlling ectoparasites in small rodents as well as interrupting or preventing the diseases caused by arthropods in small rodents, which comprise applying topical formulations, such as spot-on compositions, to the skin, or hair of the rodents.

For spot-on formulations, the pharmaceutically acceptable carrier may be a liquid carrier vehicle as described herein, and other carriers described in the art, for example in U.S. Pat. No. 6,426,333, which is incorporated herein by reference. In some embodiments, the liquid carrier vehicle can optionally contain a crystallization inhibitor such as the crystallization inhibitors described below, or mixtures thereof, to inhibit the formation of crystals or precipitate of the active components.

The veterinarily acceptable carrier will generally comprise a diluent or vehicle in which the active agents are soluble. It will be apparent to those of skill in the art that the carrier or diluent of the topical compositions must be able to deliver the active agents to the targeted location without the active agents precipitating from solution or forming crystals. In some embodiments, the carrier or diluent of the compositions will be suitable to avoid precipitation or crystallization of the active agents. In other embodiments, the compositions may include a crystallization inhibitor in addition to the carrier or diluent.

In one embodiment of the invention, the carrier for spot-on compositions may comprise diisopropyl adipate, dipropylene glycol monomethyl ether, propylene glycol monomethyl ether, 2-pyrrolidone, N-methylpyrrolidone, diethylene glycol monoethyl ether, triacetin, butyl acetate, octyl acetate, propylene carbonate, oleic acid, or a mixture of at least two of these solvents.

In another embodiment of the invention, the pharmaceutically acceptable carrier of the formulation comprises $C_1$-$C_{10}$ alcohols or esters thereof (including acetates, such as ethyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, or mixtures thereof.

In yet another embodiment, preferred solvents include $C_1$-$C_{10}$ esters of carboxylic acids such as butyl or octyl acetate.

In another preferred embodiment, the compositions of the invention that are suitable for topical administration will comprise glycerol derived carriers including glycerol monoesters (e.g. monoglycerides), glycerol diesters (e.g. diglycerides), glycerol triesters (e.g. triglycerides such as triacetin), glycerol formal, or mixtures thereof.

In another preferred embodiment, the compositions of the invention for topical administration will comprise an alcohol including ethanol or isopropanol, propylene glycol, dimethyl isosorbide (DMI), 2-pyrrolidone, N-methylpyrrolidone, dimethylsulfoxide, glycerol formal, glycol ethers including diethylene glycol monoethyl ether, diethylene glycol monomethyl ether and the like, or mixtures thereof.

In yet another preferred embodiment, the topical compositions of the invention will comprise glycerol formal, dimethyl isosorbide, N-methylpyrrolidone, diethylene glycol monoethyl ether, or mixtures thereof. In still another embodiment, the topical compositions will comprise glycerol formal, dimethyl isosorbide, or a mixture thereof.

Spot-on formulations, described for example in U.S. Pat. No. 7,262,214 (incorporated herein by reference), may be prepared by dissolving the active ingredients into the pharmaceutically or veterinary acceptable vehicle. Alternatively, the spot-on formulation can be prepared by encapsulation of the active ingredients to leave a residue of the therapeutic agent on the surface of the animal. These formulations will vary with regard to the weight of the therapeutic agent in the combination depending on the species of host animal to be treated, the severity and type of infection and the body weight of the host.

Pour-on formulations are described, for example, in U.S. Pat. No. 6,010,710, which is incorporated herein by reference. Some pour-on formulations are advantageously oily, and generally comprise a diluent or vehicle and also a solvent (e.g. an organic solvent) for the active ingredient if the latter is not soluble in the diluent. Other pour-on formulations may be in hydrophilic carriers. Pour-on formulation may be administered to livestock animals such as cattle and sheep. Typically, pour-on formulations are administered to the animal as a stripe to an external surface of the animal, e.g. a stripe from head to tail of the animal. In one embodiment, the process comprises applying the solution to livestock animals before they arrive in the Feed Lot, it being possible for this application to be the final one before the animals are slaughtered.

The compositions of the invention can also be formed in a collar such as those described in U.S. Pat. No. 5,885,607, which is incorporated herein by reference. Within the scope of the invention, matrices usually used to make collars may be used. In one embodiment of the collars which may be mentioned are matrices based on PVC (polyvinyl chloride), as described in U.S. Pat. Nos. 3,318,769; 3,852,416; 4,150,109 and 5,437,869, (all incorporated by reference) and other vinyl polymers.

The plasticizers may be chosen in particular from adipates, phthalates, phosphates and citrates. In another embodiment of the collar, one or more plasticizers are also added to the PVC, these plasticizers being chosen in particular from the following compounds: diethyl phthalate, dioctyl sebacate, dioctyl adipate, diisodecyl phthalate, acetyl tributyl citrate, diethyl hexyl phthalate, di-n-butyl phthalate, benzyl butyl phthalate, acetyl tributyl citrate, tricresyl phosphate, and 2-ethylhexyl diphenyl phosphate.

In another embodiment of the collar, a PVC matrix will be used in the presence of a primary remanent plasticizer and a secondary plasticizer, in particular according to EP 0 539 295 and EP 0 537 998.

Among the secondary plasticizers, mention may be made of the following products: acetyl triethyl citrate, triethyl citrate, triacetin, diethylene glycol monoethyl ether, triphenyl phosphate. A common stabilizer may also be added thereto.

For the purposes of the present invention, the term external device should be understood to refer to any device which can be attached externally to the animal in order to provide the same function as a collar.

Typically, the 1-arylpyrazole(s) active agents are present in the formulation at a concentration of about 1 to about 25% (w/v). In some embodiments of the invention, the 1-arylpyrazole(s) active agents are present in the formulation as a concentration from about 1 to about 20% or about 5 to about 15% (w/v). In still another embodiment of the invention, the 1-arylpyrazole active agent(s) are present in the formulation as a concentration about 8-12% (w/v).

Typically the formulations of the invention will comprise about 0.01 to about 10% (w/v) of the macrocyclic lactone active agent(s). More typically, the formulations will contain about 0.01 to about 5% or about 0.01% to about 2% (w/v) of the macrocyclic lactone active agent(s). Preferably, the formulations will contain about 0.1 to about 5% or about 0.1 to about 1% (w/v) of the macrocyclic lactone active agent(s).

The novel and inventive formulations will typically contain about 1 to about 30% (w/v) of at least one IGR compound. In other embodiments, the formulations will contain about 1 to about 20% (w/v), about 5 to about 15% (w/v) of one or more IGR compounds. More typically, the active agent is present in the formulation as a concentration about 8-12% (w/v).

The amount of the anthelmintic active agent(s) in the formulations of the invention will typically be from about 1 to about 30% (w/v). More typically, the formulations will contain from about 1 to about 20% (w/v), about 5 to about 15% (w/v) or about 8 to about 12% (w/v).

In one embodiment, the formulations of the invention will comprise about 5 to about 15% of at least one 1-arylpyrazole(s), about 0.01 to about 5% of at least one macrocyclic lactone(s), about 5 to about 15% (w/v) of at least one IGR active agent(s) and about 5 to about 15% (w/v) of at least one anthelmintic active agent(s).

In another preferred embodiment, the compositions of the invention will comprise about 5 to about 15% of at least one 1-arylpyrazole(s), about 0.01 to about 5% of at least one of abamectin, dimadectin, doramectin, emamectin, eprinomectin, ivermectin, latidectin, lepimectin, selamectin, milbemectin, milbemycin D, milbemycin oxime, moxidectin or nemadectin; about 5 to about 15% (w/v) of at least one of azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3-(2H)-one, cyromazine, chlorfluazuron, diflubenzuron, fluazuron, flucycloxuron, flufenoxuron, hexaflumuron, lufenuron, tebufenozide, teflubenzuron, triflumuron, novaluron, 1-(2,6-difluorobenzoyl)-3-(2-fluoro-4-trifluoromethyl)phenylurea, 1-(2,6-difluorobenzoyl)-3-(2-fluoro-4-trifluoromethyl)phenylurea, 1-(2,6-difluorobenzoyl)-3-(2-fluoro-4-(1,1,2,2-tetrafluoroethoxy) phenylurea or 1-(2,6-difluorobenzoyl)-3-(2-fluoro-4-trifluoromethyl)phenylurea; and about 5 to about 15% (w/v) of at least one of thiabendazole, cambendazole, parbendazole, oxibendazole, mebendazole, flubendazole, fenbendazole, oxfendazole, albendazole, cyclobendazole, triclabendazole, febantel, thiophanate and its o,o-dimethyl analogue, tetramisole, levamisole, butamisole, pyrantel, oxantel, morantel, disophenol, bephenium, thenium closylate, methyridine, pyrvinium chloride, pyrvinium pamoate, dithiazanine iodide, bitoscanate, suramin sodium, phthalofyne, miracil D, mirasan, praziquantel, clonazepam and its 3-methyl derivative, oltipraz, lucanthone, hycanthone, oxamniquine, amoscanate, niridazole, nitroxynil, hexachlorophene, bithionol, bithionol sulfoxide, menichlopholan, tribromsalan, oxyclozanide, clioxanide, rafoxanide, brotianide, bromoxanide and closantel; triclabendazole, diamfenetide, hetolin, emetine, arecoline, bunamidine, niclosamide, nitroscanate, paromomycin, paromomycin II, a depsipeptide such as emodepside, an amino acetonitrile such as monepantel, an aryloazol-2-yl cyanoethylamino compound such as N-[2-(6-bromo-2H-pyrazolo[4,3-b]pyridin-2-yl)-2-cyano-2-methylethyl]-4-trifluoromethoxybenzamide, a paraherquamide such as derquantel, or marcfortine A, B or C; in combination with a pharmaceutically acceptable carrier or diluent.

In yet another embodiment, the composition will include about 5 to about 15% (w/v) of at least one arylpyrazole(s); about 0.01 to about 5% (w/v) of at least one of eprinomectin, ivermectin, selamectin, milbemectin, milbemycin D, milbemycin oxime, or moxidectin; about 5 to about 15% (w/v) of at least one of (S)-methoprene, pyriproxyfen, hydroprene, cyromazine, fluazuron, lufenuron, or novaluron; and about 5 to about 15% (w/v) of at least one of a at least one of a benzimidazole anthelmintic, imidazothiazole anthelmintic, tetrahydropyrimidine anthelmintic, phenothiazine, piperazine, dialkylcarbamazine, ethanolamines, miracil, praziquantel, nodulisporic acid derivatives, amino acetonitrile anthelmintic, aryloazol-2-yl cyanoethylamino anthelmintic, or paraherquamide anthelmintic compound.

In still another embodiment, the compositions of the invention will comprise about 5 to about 15% (w/v) of at least one arylpyrazole(s), about 0.01 to about 2% (w/v) of at least one of eprinomectin, ivermectin, selamectin, milbemectin, milbemycin D, milbemycin oxime, or moxidectin; about 5 to about 15% (w/v) of at least one of (S)-methoprene, pyriproxyfen, hydroprene, cyromazine, fluazuron, lufenuron, or novaluron; and about 5 to about 15% (w/v) at least one of thiabendazole, cambendazole, parbendazole, oxibendazole, mebendazole, flubendazole, fenbendazole, oxfendazole, albendazole, cyclobendazole, triclabendazole, febantel, tetramisole, levamisole, pyrantel, morantel, praziquantel, closantel, triclabendazole, emodepside, an amino acetonitrile such as monepantel, an aryloazol-2-yl cyanoethylamino compound such as N-[2-(6-bromo-2H-pyrazolo[4,3-b]pyridin-2-yl)-2-cyano-2-methylethyl]-4-trifluoromethoxybenzamide, or a paraherquamide such as derquantel.

In a preferred embodiment, the compositions of the invention comprise about 5 to about 15% (w/v) of fipronil, about 0.01 to 2% (w/v) of at least one of eprinomectin, ivermectin, milbemycin oxime or moxidectin; about 5 to about 15% (w/v) of at least one of (S)-methoprene, pyriproxyfen, or lufenuron; and about 5 to about 15% (w/v) of at least one of febantel, levamisole, pyrantel, or praziquantel. In another preferred embodiment, the compositions of the invention will comprise about 8 to about 12% (w/v) of fipronil, about 0.1 to about 1% (w/v) of at least one of eprinomectin, ivermectin, milbemycin oxime or moxidectin; about 8 to about 12% (w/v) of at least one of (S)-methoprene, pyriproxyfen, or lufenuron; and about 8 to about 12% (w/v) at least one of febantel, levamisole, pyrantel, or praziquantel.

In some embodiments of the invention, an emollient and/or spreading and/or film-forming agent may be added to the topical compositions of the invention. In some embodiments the emollient and/or spreading and/or film-forming agents include:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulphonate, sodium dioctylsulphosuccinate; fatty acids (e.g. those derived from coconut oil), (c) cationic surfactants such as water-soluble quaternary ammonium salts of formula N⁺R'R"R'"R""Y⁻, in which the R radicals are optionally hydroxylated hydrocarbon radicals and Y⁻ is an anion of a strong acid such as the halide, sulfate and sulphonate anions; cetyltrimethylammonium bromide is among the cationic surfactants which can be used, (d) amine salts of formula N⁺ R'R"R'" in which the R radicals are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine, and (g) a mixture of at least two of these agents.

In one embodiment, the emollient is used in a proportion of from about 0.1 to about 10%, or about 0.25 to about 5% (w/v).

In one embodiment of the invention, the composition can be in ready-to-use solution form as is described, for example, in U.S. Pat. No. 6,395,765, which is incorporated herein by reference. In addition to the active agents, the ready-to-use solution can contain a carrier or diluent, including an organic solvent(s), and a crystallization inhibitor.

In some embodiments, the crystallization inhibitor can be present in a proportion of about 1 to about 30% (w/v). Typically, the crystallization inhibitor may be present in a proportion of about 1% to about 20% (w/v) or about 5% to about 15% (w/v). Acceptable inhibitors are those whose addition to the formulation inhibits the formation of crystals of the active agents when the formulation is applied. In some embodiments, formulations may include compounds that function as crystallization inhibitors other than those listed herein. In these embodiments, the suitability of a crystallization inhibitor may be determined by testing if it will sufficiently inhibit the formation of crystals so that a sample containing 10% (w/v) of the 1-arylpyrazole in a solvent as described above with 10% (w/v) of the crystallization inhibitor will result in less 20, preferably less than 10 crystals when placed on a glass slide at 20° C. for 24 hours.

Crystallization inhibitors which are useful for the invention include but are not limited to:

(a) polyvinylpyrrolidone, polyvinyl alcohols, copolymers of vinyl acetate and of vinylpyrrolidone, 2-pyrrolidone including N-methylpyrrolidone, dimethylsulfoxide, polyethylene glycols, benzyl alcohol, mannitol, glycerol, sorbitol or polyoxyethylenated esters of sorbitan; lecithin or sodium carboxymethylcellulose; or acrylic derivatives, such as polymers derived from acrylic monomers including polyacrylates or polymethacrylates; and, a solvent as described herein that inhibits the crystallization of the active agent, and similar compounds;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulphonate or sodium dioctyl sulphosuccinate; or fatty acids (e.g. coconut oil);

(c) cationic surfactants, such as water-soluble quaternary ammonium salts of formula N⁺ R'R"R'"R""Y⁻, in which the R radicals are identical or different optionally hydroxylated hydrocarbon radicals and Y⁻ is an anion of a strong acid, such as halide, sulfate and sulphonate anions; cetyltrimethylammonium bromide is one of the cationic surfactants which can be used;

(d) amine salts of formula N⁺R'R"R'", in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents can be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants. In another embodiment of the surface active agents, the agent is a polyoxyethylenated ester of sorbitan. In yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned above.

The volume of the topical composition applied is not restricted as long as the amount of substance administered is shown to be safe and efficacious. Typically, the volume applied depends on the size and weight of the animal as well as the concentration of active, the extent of infestation by parasites and the type of administration. For spot-on compositions, the volume applied is typically of the order of about 0.1 to about 1 ml, or about 0.1 ml to about 5 ml, or about 0.1 ml to about 10 ml. In other embodiments, the volume may be about 4 ml to about 7 ml. For larger animals, the volume may be higher including, but not limited to, up to 10 ml, up to 20 ml or up to 30 ml, or higher. In one embodiment of the volume, the volume is on the order of about 0.5 ml to about 1 ml or about 0.5 ml to about 2 ml for cats, and on the order of about 0.3 to about 3 ml or 4 ml for dogs, depending on the weight of the animal.

For the pour-on form of the composition, the volume applied can be of the order of about 0.3 to about 100 mL. In other embodiments, volume applied of the pour-on formulations may be about 1 ml to about 100 ml or about 1 ml to about 50 ml. In still other embodiments, the volume may be about 5 ml to about 50 ml or about 10 ml to about 100 ml.

Dosage forms may contain from about 0.5 mg to about 5 g of a combination of active agents. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

Methods of Treatment

In another aspect of the invention, a method for preventing or treating a parasite infestation/infection in an animal is provided, comprising administering a composition comprising an effective amount of at least one 1-arylpyrazole compound of formula (I) or (IA) in combination with at least one macrocyclic lactone active agent, at least one IGR compound, and at least one anthelmintic active agent, together with a pharmaceutically acceptable carrier. The compositions or formulations of the invention have long-lasting efficacy against ectoparasites (e.g. fleas and ticks) and are also active against endoparasites that harm animals.

In one embodiment of the invention, methods for the treatment or prevention of a parasitic infestation or infection in a domestic animal are provided, which comprise administering a composition comprising an effective amount of at least one arylpyrazole of formula (I) or (IA), at least one IGR compound, at least one macrocyclic lactone active agent and at least one anthelmintic active agent to the animal. Ectoparasites against which the methods and compositions of the invention are effective include, but are not limited to, fleas, ticks, mites, mosquitoes, flies and lice. The compositions and methods of the invention are also effective against endoparasites including, but not limited to, cestodes, nematodes, such as filariae, *Dirofilaria immitis* (heartworm), hookworms and roundworms of the digestive tract of animals and humans.

In one embodiment, the invention provides methods for the treatment and prevention of parasitic infections and infestations of animals (either wild or domesticated), including livestock and companion animals such as cats, dogs, horses, chickens, sheep, goats, pigs, turkeys and cattle, with the aim of ridding these hosts of parasites commonly encountered by such animals.

In a preferred embodiment, the invention provides methods and compositions for the treatment or prevention of parasitic infections and infestations in companion animals including, but not limited to, cats and dogs. In a particularly preferred embodiment of the invention, the methods and compositions described are used to prevent or treat parasitic infections or infestations in cats.

By "treating" or "treat" or "treatment" is intended the application or administration of a composition of the invention to an animal that has a parasitic infestation for the eradication of the parasite or the reduction of the number of the parasites infesting the animal undergoing treatment. It is noted that the compositions of the invention may be used to prevent such a parasitic infestation.

It will be appreciated by those of skill in the art that the methods of the invention encompass administering the 1-arylpyrazole compound(s), the macrocyclic lactone active agent(s), the IGR compound(s) and the anthelmintic active agent(s) together in the same carrier or diluent or separately where each active agent or mixtures of the active agents are present in their own carriers or diluents. For example when the active agents are administered topically, the 1-arylpyrazole compound(s) may be administered at the same location on the animal at the same time as the other active agents, or the 1-arylpyrazole compound(s) may be administered at a different location on the animal than the other active agents. Each active agent may be administered simultaneously or sequentially in separate carriers, which may be the same or different. Furthermore, each of the active compound(s) may be administered by the same mode of administration (e.g. topical, oral, parenteral, etc.), or the different active agents may be administered by different modes of administration.

In one embodiment of the invention, the method comprises administering each of the 1-arylpyrazole(s), the macrocyclic lactone(s), the IGR(s) and the anthelmintic(s) separately and sequentially.

In another embodiment of the invention, the method comprises administering each of the 1-arylpyrazole(s), the macrocyclic lactone(s), the IGR(s) and the anthelmintic(s) simultaneously.

In yet another embodiment of the invention, the method comprises administering each of the 1-arylpyrazole(s), the macrocyclic lactone(s), the IGR(s) and the anthelmintic(s) simultaneously in the same carrier or diluent.

In still another embodiment, the method comprises administering one or more of the active agents separately from the other active agents in a separate carrier, which may be the same or different than the carrier that is used for the other active agents.

In another aspect of the invention, a kit for the treatment or prevention of a parasitic infestation in an animal is provided, which comprises at least one 1-arylpyrazole(s), at least one macrocyclic lactone(s), at least one IGR(s) and at least one anthelmintic(s) together with a pharmaceutically acceptable carrier and a dispensing device for topical application of the composition. The dispensing device may be a pipette, syringes, roll on, droppers, capsules, foil packages, vials, twist tip containers and other single dose and multi-dose containers, which includes an effective dose of each active agent in the pharmaceutically acceptable carrier or diluent.

Additional Active Agents

Additional veterinary/pharmaceutical active ingredients may be used with the compositions of the invention. In some embodiments, the additional active agents may include, but are not limited to, acaricides, anthelmintics, anti-parasitics and insecticides. Anti-parasitic agents can include both ectoparasiticidal and endoparasiticidal agents.

Veterinary pharmaceutical agents that may be included in the compositions of the invention are well-known in the art (see e.g. *Plumb' Veterinary Drug Handbook, 5th Edition*, ed. Donald C. Plumb, Blackwell Publishing, (2005) or *The Merck Veterinary Manual, 9th Edition*, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levetiracetam, levothyroxine sodium, lidocaine, lincomycin, liothyronine sodium, lisinopril, lomustine (CCNU), lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodium thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In yet another embodiment of the invention, additional adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phos alone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfuram, isobornyl thiocyanato acetate, monosulfuram, pirenonylbutoxide, rotenone, triphenyltin acetate, triphenyltin hydroxide, deet, dimethyl phthalate, and the compounds 1,5a,6,9,9a,9b-hexahydro-4-a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An insecticidal agent that can be combined with the compound of the invention to form a composition can be a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular infection of an insect.

In certain embodiments, an insecticidal agent that can be combined with the compositions of the invention is a semicarbazone, such as metaflumizone.

In general, the additional active agent is included in the composition in an amount of between about 0.1 µg and about 1000 mg. More typically, the additional active agent may be included in a dose of about 10 µg to about 500 mg, about 1 mg to about 300 mg, about 10 mg to about 200 mg or about 10 mg to about 100 mg. In one embodiment of the invention, the additional active agent is included in a dose of between about 1 µg and about 10 mg. In other embodiments of the invention, the additional active agent may be included in a dose of about 5 µg/kg to about 50 mg/kg per weight of the animal. In other embodiments, the additional active agent may be present in a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

Optionally, a fragrance may be added to any of the compositions of the invention. Fragrances which are useful for the invention include but are not limited to:

(i) carboxylic acid esters such as octyl acetate, isoamyl acetate, isopropyl acetate and isobutyl acetate;

(ii) fragrant oils such as lavender oil.

The compositions of the invention are made by mixing the appropriate amount of the active agents, pharmaceutically acceptable carrier or diluent and optionally a crystallization inhibitor, antioxidant, preservative, film former, etc., to form a composition of the invention. Various forms (e.g. tablets, pastes, pour-on, spot-on, collars, etc.) of the composition can be obtained by following the method of making these forms described above by the description of making these forms found in general formulation text known to those in the art, e.g. *Remington—The Science and Practice of Pharmacy* (21$^{st}$ Edition) (2005), *Goodman & Gilman's The Pharmacological Basis of Therapeutics* (11$^{th}$ Edition) (2005) and *Ansel's Pharmaceutical Dosage Forms and Drug Delivery Systems* (8$^{th}$ Edition), edited by Allen et al., Lippincott Williams & Wilkins, (2005).

The inventive formulations may contain other inert ingredients such as antioxidants, preservatives, or pH stabilizers. These compounds are well known in the formulation art. Antioxidant such as an alpha tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation, with about 0.05 to about 1.0% being especially preferred.

Preservatives, such as the parabens (methylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tataric acid/tartrate, lactic acid/lactate, phosphoric acid/phosphate, glycine/glycimate, tris, glutamic acid/glutamates and sodium carbonate.

The compositions of the invention are administered in parasiticidally effective amounts which are determined by the route of administration, e.g. oral, parenteral, topical, etc. In each aspect of the invention, the compounds and compositions of the invention can be applied against a single pest or combinations thereof.

The compositions of the invention may be administered continuously, for treatment or prevention of parasitic infections or infestations. In this manner, the compositions of the invention deliver an effective amount of the active compounds to the animal in need thereof to control the target parasites. By "effective amount" is intended a sufficient amount of a composition of the invention to eradicate or reduce the number of parasites infesting the animal. In some embodiments, an effective amount of the active agent achieves at least 70% efficacy against the target parasite. In other embodiments, an effective amount of the active agent achieves at least 80%, or at least 90% efficacy against the target pests. Preferably, an effective amount of the active agent will achieve at least 95%, at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In one treatment embodiment, the treatment is carried out so as to administer to the animal, on a single occasion, a dose containing between about 0.001 and about 100 mg/kg of the active agents. In another embodiment, the composition administered delivers a dose of about 1 to 20 mg/kg of an arylpyrazole, about 1 to 20 mg/kg of an IGR, about 0.01 to 5 mg/kg of a macrocyclic lactone active agent, and about 1 to 20 mg/kg of an anthelmintic compound. In a preferred embodiment, the compositions of the invention will deliver about 5 to 15 mg/kg of an arylpyrazole, about 5 to 15 mg/kg of an IGR, about 0.1 to 1 mg/kg of a macrocyclic lactone and about 5 to about 15 mg/kg of an anthelmintic compound.

Higher amounts may be provided for very prolonged release in or on the body of the animal. In another treatment embodiment, the amount of active agents for birds and other animals which are small in size is greater than about 0.01 mg/kg, and in another embodiment for the treatment of small-sized birds and other animals, the amount of is between about 0.01 and about 20 mg/kg of weight of animal.

The solutions according to the invention may be applied using any means known per se, e.g. using an applicator gun or a metering flask, pipette, syringes, roll on, droppers, capsules, foil packages, vials, twist tip containers and other single dose and multi-dose containers, In one preferred embodiment of the method of use in cats, a composition comprising a 1-arylpyrazole compound, a macrocyclic lactone, an IGR and an anthelmintic compound has an efficacy against fleas of at least about 80.0% or higher for at least about 43 days, at least about 50 days, at least about 57 days, or at least about 63 days. In another embodiment of this method of use in cats, a composition comprising a 1-arylpyrazole compound, a macrocyclic lactone, an IGR and an anthelmintic compound has an efficacy against fleas of at least 90.0% or higher for at least about 43 days, at least about 50 days, or at least about 57 days. In yet another embodiment of the invention for the treatment of cats, a composition comprising a 1-arylpyrazole compound, a macrocyclic lactone, an IGR and an anthelmintic compound has an efficacy against fleas of at least about 95% or higher for at least about 36 days, at least about 43 days or at least about 54 days.

In another embodiment for the treatment of cats, a composition of the invention comprising a 1-arylpyrazole compound, a macrocyclic lactone, an IGR and an anthelmintic compound has an efficacy of at least about 90% against ticks for at least about 30 or 37 days. In another embodiment for the treatment of cats, a composition comprising a 1-arylpyrazole compound, a macrocyclic lactone, an IGR and an anthelmintic compound has an efficacy of at least about 95% against ticks for at least 30 days or 37 days. In each of these embodiments of use against fleas and ticks, the arylpyrazole compound may be fipronil; the macrocyclic lactone compound may be ivermectin, eprinomectin or moxidectin; the IGR is (S)-methoprene, pyriproxyfen, hydroprene, cyromazine, fluazuron, lufenuron, or novaluron; and the anthelmintic compound is levamisole, febantel, pyrantel or praziquantel.

In another embodiment for the treatment of cats, the composition comprising a 1-arylpyrazole compound, a macrocyclic lactone, an IGR and an anthelmintic compound has an efficacy of at least 90% at inhibiting the larval hatching of fleas for at least about 47 days, at least about 54 days or at least about 61 days.

In yet another embodiment for the treatment of cats, a composition of the invention comprising a 1-arylpyrazole compound, a macrocyclic lactone, an IGR and an anthelmintic compound has an efficacy of at least 90% against endoparasites including *Dipylidium caninum* and *Taenia taeniaeformis*. In another embodiment for the treatment of cats, a composition of the invention has an efficacy of 100% against *Taenia taeniaeformis*.

In another embodiment for the treatment of cats, a composition comprising a 1-arylpyrazole compound, a macrocyclic lactone, an IGR and an anthelmintic compound has an efficacy of at least 85%, at least 90%, at least 95% or 100% against *Toxocara cati* (roundworm).

In another embodiment for the treatment of cats, a composition of the invention comprising a 1-arylpyrazole compound, a macrocyclic lactone, an IGR and an anthelmintic compound has an efficacy of 100% against *Ancylostoma tubaeforme* (hookworm).

In another embodiment for the treatment of cats, a composition of the invention comprising a 1-arylpyrazole compound, a macrocyclic lactone, an IGR and an anthelmintic compound has an efficacy of 100% against *Dirofilaria immitis* (heartworm).

In another embodiment for the treatment of cats, a composition of the invention comprising a 1-arylpyrazole compound, a macrocyclic lactone, an IGR and an anthelmintic compound has proven safe for use in cats with adult *Dirofilaria immitis* (heartworm) infection.

In one embodiment of the location of administration, a single formulation containing the active agent in a substantially liquid carrier and in a form which makes possible a single application, or an application repeated a small number of times, will be administered to the animal over a localized region of the animal, e.g. between the two shoulders. In one embodiment of the invention, the localized region has a surface area of about 10 cm$^2$ or larger. In another embodiment of the invention, the localized region has a surface are of between about 5 and about 10 cm$^2$ area.

EXAMPLES

The invention is further described by the following non-limiting examples which further illustrate the invention, and are not intended, nor should they be interpreted to, limit the scope of the invention.

Example 1

Efficacy Against Fleas

The efficacy of a spot-on composition of the invention comprising fipronil, (S)-methoprene, eprinomectin and praziquantel in a pharmaceutical or veterinary acceptable liquid carrier against adult fleas (*Ctenocephalides felis*), egg and larvae in cats was studied. The compositions contained fipronil and (S)-methoprene at concentrations to deliver a dose of 10 mg/kg fipronil and 12 mg/kg (S)-methoprene to cats infested with adult fleas. It was demonstrated that at volumes of 0.10, 0.15 and 0.20 ml/kg and different concentration of active agents, the efficacy of the formulations was not affected.

All cats were infected with a defined number of fleas (e.g. 100) prior to treatment with the compositions. At day 0, cats were treated with the composition, except for a control group. On day 1, all cats were combed for the removal and counting of live fleas. Cats were subsequently infected weekly with a defined number of fleas (e.g. 100). All cats were combed for the removal and counting of live fleas weekly, 24 hours after being infected with fleas to determine the efficacy of the compositions over time. The efficacy or percentage reduction of a treatment is calculated at any given timepoint by comparing the mean number of fleas in the treated group with the mean number of fleas in the control group. The early timepoint (Day 1) allows the assessment of the onset of efficacy; the weekly timepoints allow the assessment of the duration of efficacy.

Table 1 shows the efficacy (% reduction) of a spot-on composition of the invention containing fipronil, (S)-methoprene, eprinomectin and praziquantel in glycerol formal and dimethyl isosorbide at concentrations to deliver 10 mg/kg fipronil, 12 mg/kg (S)-methoprene, 0.5 mg/kg eprinomectin and 10 mg/kg praziquantel to cats infested with adult fleas (*Ctenocephalides felis*). The volume of the composition administered was 0.2 mL/kg per weight of the animal.

TABLE 1

| | Efficacy against adult fleas (% reduction) | | | | | | | |
|---|---|---|---|---|---|---|---|---|
| | Day 1 | Day 3 | Day 15 | Day 22 | Day 29 | Day 36 | Day 43 | Day 50 |
| % reduction | 96.1 | 99.8 | 99.9 | 98.1 | 99.3 | 99.6 | 98.3 | 91.6 |

In another study, the effectiveness of the composition against adult fleas and their ability to inhibit the development of flea eggs and larvae were studied. The effectiveness against adult fleas was tested as described above in Example 1 up to day 29, after which the efficacy was assessed four days after each infestation. During a 4-day period after infestation with fleas, produced flea eggs falling off the cats were collected, counted and incubated. Following defined incubation periods (about 3 days for larval hatching assessment and about 35 days for adult emergence assessment), the proportion of hatches larvae and/or emerged adults in the treated group are compared with the proportion of hatched larvae and/or emerged adults in the control group. Table 2 shows the larval hatching inhibition of the composition described for Table 1 above. As a result of the superior efficacy of the composition, no flea eggs appeared prior to this day 43 of the study. Efficacy of at least 90% for inhibiting larval hatching was demonstrated for 2 weeks after adulticidal effect alleviation, i.e. when flea eggs start to appear on day 43.

TABLE 2

| | Larval Hatching Inhibition | | | | | |
|---|---|---|---|---|---|---|
| | Day 1 | Day 15 | Day 22 | Day 29 | Day 36 | Day |
| % reduction adult fleas | 93.7 | 99.4 | 99.7 | 98.8 | 99.6 | 98.3 91.6 |
| | | | | | Up to Day 47 | Day 54 | Day 61 |
| Larval hatching inhibition (%) | | | | | 100 | 99.2 | 91.1 |

Table 3 below shows the efficacy of a spot-on composition of the invention containing fipronil, (S)-methoprene, eprinomectin and praziquantel in a pharmaceutically acceptable carrier (mixture of glycerol formal and dimethyl isosorbide) at concentrations to deliver 10 mg/kg fipronil, 9 mg/kg (S)-methoprene, 0.4 mg/kg eprinomectin and 8 mg/kg praziquantel at volumes of 0.10 mL/kg per weight of animal.

TABLE 3

| | | Efficacy against adult fleas (%) | | | | | | | | |
|---|---|---|---|---|---|---|---|---|---|---|
| | Volume (mL/kg) | Day 1 | Day 15 | Day 22 | Day 29 | Day 36 | Day 43 | Day 50 | Day 57 | Day 63 |
| % reduction | 0.15 | 96.6 | 99.9 | 99.6 | 97.5 | 98.9 | 99.2 | 98.0 | 96.4 | 88.4 |
| | 0.10 | 96.7 | 99.8 | 99.1 | 97.4 | 97.7 | 99.5 | 97.8 | 97.9 | 99.9 |

Example 2

Efficacy Against Ticks

The efficacy of a composition of the invention comprising fipronil, (S)-methoprene, eprinomectin and praziquantel in a pharmaceutically acceptable carrier (mixture of glycerol formal and dimethyl isosorbide) against ticks was studied. The composition contained concentrations of the actives to deliver 10 mg/kg fipronil, 12 mg/kg (S)-methoprene, 0.45 mg/kg eprinomectin and 10 mg/kg praziquantel at a volume of 0.10 mL/kg per weight of animal. Cats were infected with a defined number of ticks (e.g. 50 females, Ixodes ricinus) before treatment. At day 0, all cats were treated with a composition comprising fipronil, (S)-methoprene, eprinomectin and praziquantel in glycerol formal and dimethyl isosorbide. On day 2, attached or free ticks are removed from each cat, and live ticks were counted. Weekly afterwards, all cats were infested with defined number of ticks (e.g. 50 females), and attached and free ticks were removed and counted 48 hours afterward. Table 4 below shows the efficacy (% reduction) of the composition against ticks.

TABLE 4

Efficacy against ticks (% reduction)

|  | Day 2 | Day 9 | Day 16 | Day 23 | Day 30 | Day 37 |
|---|---|---|---|---|---|---|
| % reduction | 97.2 | 100 | 99.7 | 98.8 | 98.8 | 97.6 |

Example 3

Efficacy Against Endoparasites

The efficacy of compositions comprising (S)-methoprene, eprinomectin and praziquantel in a pharmaceutically acceptable carrier (mixture of glycerol formal and dimethyl isosorbide) against endoparasites was studied. The compositions contained concentrations of the actives to deliver 10 mg/kg fipronil, 12 mg/kg (S)-methoprene, and different doses of eprinomectin and praziquantel.

Cats were infected with infective materials (eggs, larvae) of the target parasite before treatment. Cats were screened and selected for the study based on positive target parasite diagnosis (e.g. egg identification in feces). Alternatively, cats positive for the target parasite were sourced and confirmed to be infected with the parasite (e.g. egg identification in feces). On day 0, cats were treated with the composition tested, except for the control group. On approximately day 7-10 (time necessary for parasite to die and to be eliminated from the body), cats were necropsied for parasite recovery and count. The efficacy or percentage reduction of the treatment is calculated by comparing the mean number of live target parasites in the treated group with the mean number of live target parasites in the control group.

Compositions comprising praziquantel to deliver doses of 6, 8 or 10 mg/kg were tested against Dipylidium caninum in 3 studies. The efficacy of compositions comprising praziquantel was also tested against T. taeniaeformis and T. cati at certain doses. Table 5 below shows the efficacy of compositions comprising fipronil at a dose of 10 mg/kg, (S)-methoprene at 12 mg/kg, and eprinomectin and praziquantel at varying doses against these three endoparasites.

TABLE 5

Efficacy against endoparasite

| | | | % Reduction | | |
|---|---|---|---|---|---|
| Study | Praziquantel Dose (mg/kg) | Eprinomectin Dose (mg/kg) | D. caninum | T. taeniaeformis | T. cati |
| 1 | 6 | 2.5 | 64 | 100 | ne |
|  | 8 | 2.5 | 78 | 100 | ne |
|  | 10 | 2.5 | 92 | 100 | ne |
| 2 | 8 | 0.5 | 98 | ne | 95 |
|  | 10 | 0.5 | 98 | ne | 87 |
| 3 | 10 | 0.25 | 100 | ne | 95 |
|  | 10 | 0.5 | 91 | ne | 100 | ne = not evaluated

Example 4

Effect of Eprinomectin Dose Against Endoparasites

In 12 separate studies, the effectiveness of compositions comprising fipronil, (S)-methoprene, praziquantel and varying doses of eprinomectin against various endoparasites were studied. The compositions contained concentrations of fipronil, (S)-methoprene and praziquantel to deliver doses of 10 mg/kg, 12 mg/kg and 10 mg/kg, respectively, of each active. The concentration of eprinomectin was varied to deliver doses of between 0.1 mg/kg to 10 mg/kg. Cats infected naturally or experimentally with A. tubaeforme (hookworm), T. cati (roundworm), D. caninum and different strains of D. immitis (heartworm) were used in the study. The results of the 12 studies are presented in Table 6 below.

TABLE 6

Efficacy against endoparasites

| | % Reduction Worm Type | | | | | |
|---|---|---|---|---|---|---|
| | Hook[1] | Round[2] | Round[2] | Round[2] | Hook[1] | Round[3] |
| | Infection Type | | | | | |
| | Exp. | Exp. | Exp. | Exp. | Exp. | Nat. |
| Eprinomectin Dose (mg/kg) | | | | | | |
| 10 | 100 | 100 | — | — | — | — |
| 2.5 | 100 | 100 | — | — | — | — |
| 1.0 | — | — | 100 | — | — | — |
| 0.5 | — | — | 100 | 97 | 100 | 92 |
| 0.35 | — | — | — | 96 | 100 | — |
| 0.25 | — | — | — | — | — | — |
| 0.2 | — | — | — | 92 | 100 | — |
| 0.1 | — | — | — | 73 | 100 | — |

[1] A. tubaeforme,
[2] T. cati,
[3] mixed D. caninum/T. cati

Table 7 shows the effect of doses of eprinomectin of between 0.1 mg/kg to 0.5 mg/kg against roundworm, including a new strain of T. cati and against two strains of heartworm (D. immitis). Although the number of non-treated cats (controls) infected with D. immitis was insufficient (2/10) to calculate a percent reduction, the lowest dose of eprinomectin was shown to be effective against both strains of heartworm.

TABLE 7

| | % Reduction Worm Type | | | | | |
|---|---|---|---|---|---|---|
| | Round[4] | Round[2] | Round[5] Infection Type | Hook[6] | HW[7] | HW[8] |
| | Exp. | Nat. | Exp. | Exp. | Exp. | Nat. |
| Eprinomectin Dose (mg/kg) | | | | | | |
| 0.5 | — | 100 | 100 | 100 | 0/10 | 0/10 |
| 0.4 | 100 | — | — | — | — | — |
| 0.25 | — | 95 | — | — | — | — |
| 0.2 | 99.5 | — | 98 | 100 | — | — |
| 0.1 | — | — | — | — | 0/10 | 0/10 |

[4]new strain of *T. cati*,
[2]*T. cati*,
[5]immature stage of *T cati*,
[6]immature stage of *A. tubaeforme*,
[7]*D. immitis* EU strain,
[8]*D. immitis* US strain In another study, the number of non-treated cats (controls) infected with a US strain of *D. immitis* was sufficient (12/14) to calculate the percent reduction, which was 100% (0/14).

Example 5

Stability of Formulation at 30° C.

As discussed above, it is surprising that the formulations of the present invention having at least one 1-arylpyrazole, at least one macrocyclic lactone, at least one IGR and at least one anthelmintic compound with substantially different physicochemical properties, including solubility and solvent compatibility, could be successfully formulated into a stable composition in one pharmaceutically acceptable carrier system. The stability of each active in a preferred composition of the invention comprising fipronil, (S)-methoprene, eprinomectin and praziquantel in a carrier comprising glycerol formal and dimethyl isosorbide was evaluated at 30° C. using high performance liquid chromatography (HPLC). The study demonstrated that each active in the composition was stable in solution for up to 24 months at 30° C. in the presence of the other compounds (see the FIGURE).

As the non-limiting examples above demonstrate, the compositions of the invention comprising at least one arylpyrazole active agent, at least one macrocyclic lactone, at least one IGR and at least one anthelmintic compound show superior long lasting efficacy against both ectoparasites and endoparasites in a mammal (cat).

The invention is further described by the following numbered paragraphs:

1. A topical veterinary composition for treating or preventing a parasitic infection or infestation in an animal comprising:

(a) a combination of at least one 1-arylpyrazole active agent, at least one macrocyclic lactone active agent, at least one insect growth regulator active agent, and at least one anthelmintic active agent;

(b) a pharmaceutically acceptable carrier; and (c) optionally a crystallization inhibitor.

2. The topical veterinary composition of paragraph 1, wherein the 1-arylpyrazole active agent has the formula (I)

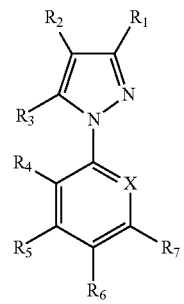

wherein:

$R_1$ is hydrogen, cyano, nitro, halogen, $R_3$, $R_8$, formyl, —C(O)$R_8$, —C(O)O$R_8$, —C(O)N$R_9R_{10}$, —C(=NOH)NH$_2$, —C(=NNH$_2$)$R_9$, or —C(S)NH$_2$;

$R_2$ is $R_8$, halogen, cyano, nitro, —SCN, 4-5-dicyanoimidazol-2-yl, or —S(O)$_m R_{11}$;

$R_3$ is hydrogen, halogen, alkyl, haloalkyl, OH, O$R_8$, S(O)$_m R_{11}$, —C(O)$R_8$, —C(O)O$R_8$, N$R_9R_{10}$, —N=C($R_9$) ($R_{14}$), —N=C($R_{10}$)—Z—($R_9$), —N=C($R_{10}$)—N$R_9R_{10}$, —N($R_8$)—C($R_{10}$)=N$R_9$, —N($R_{11}$)C(O)CR$_{15}R_{10}R_{11}$, —N($R_{11}$)C(O)aryl, —N($R_{11}$)C(O)heteroaryl or —N($R_{11}$)C(O)O$R_{10}$;

$R_4$, $R_5$ and $R_7$ are independently hydrogen, halogen, alkyl, haloalkyl, cyano or nitro;

$R_6$ is halogen, alkyl, haloalkyl, alkoxy, haloalkyloxy, cyano, nitro, —C(O)$R_{12}$, —S(O)$_6 R_{12}$ or SF$_5$;

X is a nitrogen atom or C—$R_{13}$;

Z is O, S(O)$_m$ or N$R_9$ $R_8$ is alkyl or haloalkyl;

$R_9$ is hydrogen, alkyl, haloalkyl or alkoxy;

$R_{10}$ is hydrogen, alkyl, haloalkyl, alkoxy, or —C(O)$R_8$;

$R_{11}$ is alkyl, haloalkyl, alkenyl, haloalkenyl, alkynyl, haloalkynyl, alkoxyalkyl, or haloalkoxyalkyl;

$R_{12}$ is alkyl or haloalkyl;

$R_{13}$ is hydrogen, halogen, cyano, nitro, alkyl, haloalkyl, alkoxy or haloalkoxy;

$R_{14}$ is optionally substituted aryl or optionally substituted heteroaryl;

$R_{15}$ is hydrogen, halogen, alkoxy, haloalkoxy, alkoxyalkyl, haloalkoxyalkyl, formyloxy, alkylcarbonyloxy, haloalkylcarbonyloxy, althilthio, haloalkylthio, alkylsulfinyl, haloalkylsulfinyl, alkylsulfonyl, haloalkylsulfonyl, alkylamino, dialkylamino, haloalkylamino, di(haloalkyl)amino, aryloxy or arylalkoxy;

wherein said alkyl, haloalkyl, alkoxy, groups are optionally substituted with alkyl, haloalkyl, alkoxy, aryl, or heteroaryl; said aryl or heteroaryl groups are optionally substituted with one or more of alkyl, haloalkyl, aryl, halogen, C(O)$R_8$, —C(O)O$R_8$, —C(O)N$R_9R_{10}$, —C(S)NH$_2$, or —S(O)$_m R_{11}$ m is 0, 1 or 2; and n is 0, 1 or 2; or a pharmaceutically acceptable salt, hydrate or solvate thereof 3. The topical veterinary composition of paragraph 2, wherein:

$R_1$ is cyano, —C(O)$R_8$, —C(O)O$R_8$, —C(O)N$R_9R_{10}$, —C(=NOH)NH$_2$, —C(=NNH$_2$)$R_9$, or —C(S)NH$_2$;

$R_2$ is —SCN, 4-5-dicyanoimidazol-2-yl, or —S(O)$_m R_{11}$; and $R_3$ is alkyl, haloalkyl or N$R_9R_{10}$.

4. The topical veterinary composition of paragraph 2, wherein:

$R_1$ is cyano;

$R_2$ is —S(O)$_m R_{11}$;

$R_3$ is $C_1$-$C_4$alkyl, $C_1$-$C_4$haloalkyl, or $NR_9R_{10}$;
$R_4$, $R_5$ and $R_7$ are independently hydrogen, or halogen;
$R_6$ is halogen, $C_1$-$C_4$alkyl, $C_1$-$C_4$haloalkyl, or $SF_5$;
X is C—$R_{13}$; and
$R_{13}$ is halogen or $C_1$-$C_4$haloalkyl.

5. The topical veterinary composition of paragraph 1, wherein the 1-arylpyrazole active agent has the formula (Ia)

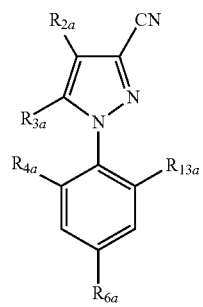

wherein:
$R_{2a}$ is —$S(O)_mR_{11a}$;
$R_{3a}$ is methyl, ethyl or $C_1$-$C_4$ haloalkyl;
$R_{4a}$ is halogen;
$R_{6a}$ is $C_1$-$C_4$ alkyl or haloalkyl;
$R_{13a}$ is halogen;
$R_{11a}$ is $C_1$-$C_4$ haloalkyl; and
m is 0, 1 or 2; or a pharmaceutically acceptable salt, hydrate or solvate thereof.

6. The topical veterinary composition of paragraph 1, wherein the 1-arylpyrazole active agent is fipronil.

7. The topical veterinary composition of paragraph 1, wherein the at least one macrocyclic lactone active agent is an avermectin or milbemycin.

8. The topical veterinary composition of paragraph 7, wherein the avermectin or milbemycin is eprinomectin, ivermectin, selamectin, milbemectin, milbemycin D, milbemycin oxime, or moxidectin.

9. The topical veterinary composition of paragraph 1, wherein the at least one insect growth regulator is (S)-methoprene, pyriproxyfen, hydroprene, cyromazine, fluazuron, lufenuron, or novaluron.

10. The topical veterinary composition of paragraph 1, wherein the at least one anthelmintic active agent is thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, or an aryloazol-2-yl cyanoethylamino active agent.

11. The topical veterinary composition of paragraph 1, wherein the pharmaceutically acceptable carrier is a $C_1$-$C_{10}$ alcohol or ester, a $C_{10}$-$C_{18}$ saturated fatty acid or esters, a $C_{10}$-$C_{18}$ monounsaturated fatty acid or ester, a monoester or diester of an aliphatic diacid, a glycerol monoesters, a glycerol diester, a glycerol triester, a glycol, a glycol ether, a glycol ester, a glycol carbonate, a polyethylene glycol, a polyethylene glycol monoether, a polyethylene glycol diether, a polyethylene glycol monoester, a polyethylene glycol diester, or a mixture thereof.

12. The topical veterinary composition of paragraph 1, wherein the pharmaceutically acceptable carrier is acetone, acetonitrile, benzyl alcohol, ethanol, isopropanol, diisobutyl adipate, diisopropyl adipate, glycerol formal, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, dimethyl isosorbide, 2-pyrrolidone, N-methylpyrrolidone, diethylene glycol monoethyl ether, triacetin, butyl acetate, octyl acetate, propylene carbonate, butylene carbonate, dimethyl sulfoxide, dimethylformamide, dimethylacetamide, or any combination thereof.

13. The topical veterinary composition of paragraph 1, wherein the pharmaceutically acceptable carrier is triacetin, glycerol formal, diethylene glycol monoethyl ether, dimethyl isosorbide, or mixtures thereof.

14. The topical veterinary composition of paragraph 1, wherein the at least one 1-arylpyrazole is fipronil, the at least one macrocyclic lactone is eprinomectin, ivermectin, selamectin, milbemectin, milbemycin D, milbemycin oxime, or moxidectin; the at least one IGR is (S)-methoprene, pyriproxyfen, hydroprene, cyromazine, fluazuron, lufenuron, or novaluron; and the at least one anthelmintic is thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, an aryloazol-2-yl cyanoethylamino active agent.

15. The composition of paragraph 1 or paragraph 13, wherein the at least one 1-arylpyrazole is fipronil, the at least one macrocyclic lactone is eprinomectin; the at least one IGR is (S)-methoprene; and at least one anthelmintic is praziquantel.

16. The topical veterinary composition of paragraph 1 or 15, wherein the composition is in the form of a spot-on or a pour-on formulation.

17. A method for the treatment or prevention of a parasitic infestation or infection in an animal comprising administering to the animal in need thereof an effective amount of the topical veterinary composition of paragraph 1.

18. The method of paragraph 17, wherein the at least one 1-arylpyrazole is fipronil, the at least one macrocyclic lactone is eprinomectin, ivermectin, or moxidectin; the at least one IGR is (S)-methoprene or pyriproxyfen; and at least one anthelmintic is febantel, pyrantel or praziquantel.

19. The method of paragraph 17, wherein the parasite is an ectoparasite.

20. The method of paragraph 17, wherein the parasite is an endoparasite.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:
1. A topical veterinary composition for treating or preventing a parasitic infection or infestation in an animal comprising:
 (a) a combination of four active agents comprising,
  i. two contact-acting active agents, wherein one of the contact-acting active agents is fipronil and the other of the contact-acting active agents is an insect growth regulator active agent selected from the group consisting of (S)-methoprene, pyriproxyfen, hydroprene, cyromazine, fluazuron, lufenuron and novaluron; and
  ii. two systemically-acting active agents, wherein one of the systemically-acting active agents is praziquantel and the other of the systemically-acting active agents is a macrocyclic lactone active agent selected from the group consisting of eprinomectin, ivermectin, selamectin, milbemectin, milbemycin D, milbemycin oxime and moxidectin;

(b) a pharmaceutically acceptable carrier comprising dimethylisosorbide and glycerol formal; and (c) optionally a crystallization inhibitor;

wherein said composition is a liquid for topical administration;

wherein fipronil is present in a concentration of about 5 to about 15% (w/v), the insect growth regulator active agent is present in a concentration of about 5 to about 15% (w/v), the macrocyclic lactone active agent is present in a concentration of about 0.01 to about 2% and praziquantel is present in a concentration of about 5 to about 15% (w/v); and wherein the composition exhibits broad spectrum efficacy against endoparasites and ectoparasites.

2. The topical veterinary composition of claim 1, wherein the macrocyclic lactone active agent is eprinomectin, ivermectin, selamectin, milbemycin oxime, or moxidectin.

3. The topical veterinary composition of claim 1, wherein the insect growth regulator active agent is (S)-methoprene, pyriproxyfen, lufenuron, or novaluron.

4. The topical veterinary composition of claim 1, wherein the macrocyclic lactone active agent is eprinomectin, ivermectin, selamectin, milbemycin oxime, or moxidectin; and the insect growth regulator active agent is (S)-methoprene, pyriproxyfen, lufenuron, or novaluron.

5. The composition of claim 4, wherein the macrocyclic lactone active agent is eprinomectin; and the insect growth regulator active agent is (S)-methoprene.

6. The composition of claim 5, wherein:

fipronil is present at a concentration of about 8 to about 12% (w/v);

eprinomectin is present at a concentration of about 0.1 to about 1% (w/v);

(S)-methoprene is present at a concentration of about 8 to about 12% (w/v); and praziquantel is present at a concentration of about 8 to about 12% (w/v).

7. The composition of claim 1, 4 or 6, wherein the composition is a spot-on composition.

8. The composition of claim 1, wherein the composition is a pour-on composition.

9. The composition of claim 1, wherein the composition further comprises about 0.01% to about 2.0% (w/w) of an antioxidant selected from the group consisting of an alpha tocopherol, ascorbic acid, ascorbyl palmitate, fumaric acid, malic acid, sodium ascorbate, sodium metabisulfate, n-propyl gallate, butylated hydroxy anisole, butylated hydroxy toluene and monothioglycerol.

* * * * *